(12) United States Patent
Burgoon et al.

(10) Patent No.: US 8,450,332 B2
(45) Date of Patent: May 28, 2013

(54) LIMK2 INHIBITORS, COMPOSITIONS COMPRISING THEM, AND METHODS OF THEIR USE

(75) Inventors: Hugh Alfred Burgoon, Strongsville, OH (US); Nicole Cathleen Goodwin, Pennington, NJ (US); Bryce Alden Harrison, Hamilton, NJ (US); Jason Patrick Healy, Flemington, NJ (US); Ying Liu, Lawrenceville, NJ (US); Ross Mabon, Lambertville, NJ (US); Brett Marinelli, Hamilton, NJ (US); David Brent Rawlins, Morrisville, PA (US); Dennis Stewart Rice, The Woodlands, TX (US); Norris Andrew Whitlock, The Woodlands, TX (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 13/486,122

(22) Filed: Jun. 1, 2012

(65) Prior Publication Data

US 2012/0329818 A1    Dec. 27, 2012

Related U.S. Application Data

(63) Continuation of application No. 12/426,661, filed on Apr. 20, 2009, now Pat. No. 8,193,202.

(60) Provisional application No. 61/046,602, filed on Apr. 21, 2008.

(51) Int. Cl.
*A01N 43/60* (2006.01)
*A61K 31/519* (2006.01)

(52) U.S. Cl.
USPC ...................................... 514/265.1

(58) Field of Classification Search
None
See application file for complete search history.

(56) References Cited

U.S. PATENT DOCUMENTS

| | | |
|---|---|---|
| 6,635,762 B1 | 10/2003 | Blumenkopf |
| 6,686,366 B1 | 2/2004 | Castelhano |
| 7,115,741 B2 | 10/2006 | Levy |
| 7,253,166 B2 | 8/2007 | Ding |
| 7,253,286 B2 | 8/2007 | Funahashi |
| 7,312,226 B2 | 12/2007 | Bashyam |
| 7,423,043 B2 | 9/2008 | Rawlins |
| 7,951,941 B2 | 5/2011 | Bednarz |
| 8,193,202 B2 | 6/2012 | Burgoon |
| 2005/0203107 A1 | 9/2005 | Bailey et al. |
| 2008/0076774 A1 | 3/2008 | Anand |
| 2009/0042893 A1 | 2/2009 | Harrison |

FOREIGN PATENT DOCUMENTS

| | | |
|---|---|---|
| WO | WO 2005020921 | 3/2005 |
| WO | WO 2006061304 | 6/2006 |
| WO | WO 2007125310 | 11/2007 |
| WO | WO 2007125315 | 11/2007 |
| WO | WO 2007125321 | 11/2007 |
| WO | WO 2007125325 | 11/2007 |
| WO | WO 2008075110 | 12/2007 |
| WO | WO 2008046023 | 5/2008 |
| WO | WO 2008048024 | 5/2008 |
| WO | WO 2008075109 | 6/2008 |

OTHER PUBLICATIONS

Amarnath and Madhav, Synthesis 837 (1974).
Birrell, GB, et al., J. Cellular Physiol. 141:74-84 (1989).
Choi et al., Bioorg. Med. Chem. Lett. 16:2173-2176 (2006).
Choi et al., Bioorg. Med. Chem. Lett. 16:2689-2692 (2006).
Foloppe et al., J. Med. Chem. 48-4332-4345 (2005).
Gangjee et al. J. Med. Chem. 49:1055-1065 (2006).
Girgis et al., Synthesis 101 (1985).
Kaufman et al., Curr. Top. Eye Res. 4:97-138 (1984).
Kaufman et al., Exp. Eye. Res. 44(2):283-91 (1987).
Kaufman et al., Invest. Ophthal. Vis. Science 37:3 Abstract 938 (1996).
Kempson et al., Bioorg. Med. Chem. 15:1829-1833 (2005).
O'Brien et al., Curr Eye Res. 18(9);985-90 (1996).
O'Brien et al., Exp. Eye. Res, 65(4):471-83 (1997).
Peterson et al., Invest. Ophthal. Vis. Science 37:3 Abstract 3803 (1996).
Seela and Peng J. Org. Chem. 71:81-90 (2006).
Smalley et al., Bioorg. Med. Chem. Lett. 18:2091-2094 (2008).
Tian et al., Arch. Ophthalmol. 116(5):633-43 (1998).
Traxler et al. Med. Res. Rev. 21:499-512 (2001).
Volberg et al., Cell. Moth. Cytoskeleton 28(4):321-36 (1994).
Wamhoff and Wehling, Synthesis 51 (1976).
Weiderholt et al., Ophthalmologica, 211(3):153-60 (1997).
West J. Org. Chem. 26:4959 (1961).
Written Opinion of the ISR issued in corresponding international application No. PCT/US2009/041126, dated Aug. 4, 2009.

*Primary Examiner* — Jeffrey Murray
(74) *Attorney, Agent, or Firm* — Max Bachrach

(57) ABSTRACT

Inhibitors of LIM kinase 2 are disclosed, along with pharmaceutical compositions comprising them and methods of their use. Particular compounds are of the formula:

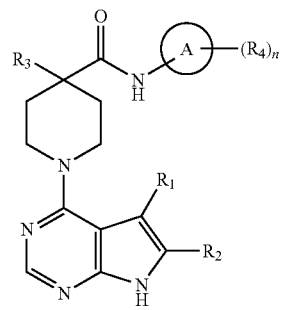

7 Claims, 1 Drawing Sheet

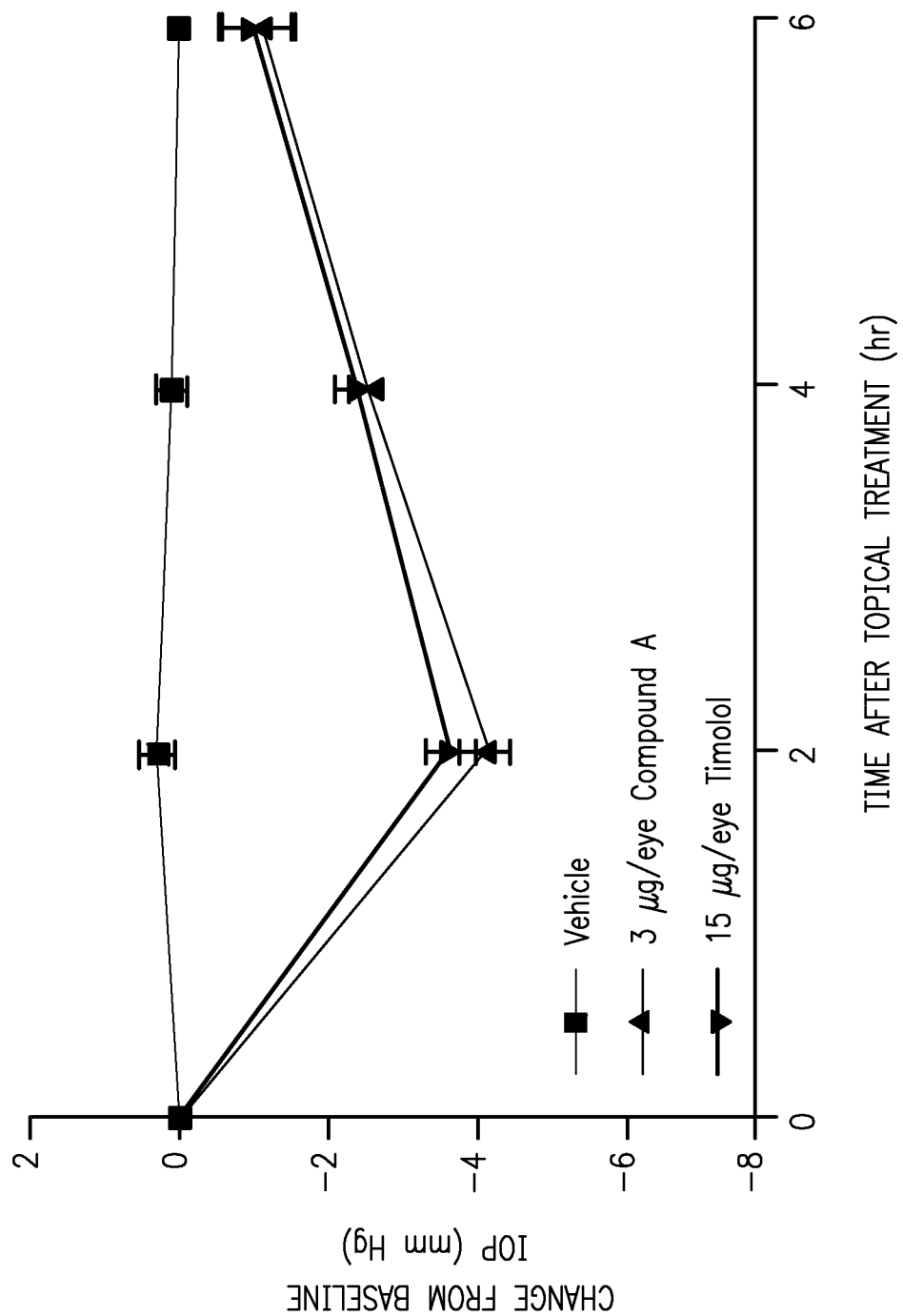

LIMK2 INHIBITORS, COMPOSITIONS COMPRISING THEM, AND METHODS OF THEIR USE

This is a continuation of U.S. application Ser. No. 12/426,661, filed Apr. 20, 2009, which claims priority to U.S. provisional patent application No. 61/046,602, filed Apr. 21, 2008, the entireties of which are incorporated herein by reference.

1. FIELD OF THE INVENTION

This invention relates to kinase inhibitors, compositions comprising them, and methods of their use to treat various diseases and disorders.

2. BACKGROUND

Protein kinases are a class of enzymes that catalyze the transfer of the γ-phosphate group from ATP to a recipient protein. The human genome is estimated to encode in excess of 500 distinct protein kinases, of which many have been implicated in a wide range of diseases and disorders, including cancer and inflammation.

The LIM kinases (LIMK) have been linked to the p53 pathway. See, e.g., International Application No. WO 02/099048. LIMK belongs to a small subfamily of kinases with a unique combination of two N-terminal LIM motifs and a C-terminal protein kinase domain. These LIM motifs and kinase domains are linked by a proline- and serine-rich region containing several putative casein kinase and map kinase recognition sites. LIM kinases and their pathway proteins are believed to contribute to Rho-induced reorganization of the actin cytoskeleton. Id. Members of the LIM kinase family include LIM kinase 1 (LIMK1) and LIM kinase 2 (LIMK2). Both phosphorylate cofilin and regulates Rho family-dependent actin cytoskeletal rearrangement. Id.

LIM kinase inhibitors have been proposed for the treatment of cancer. Id. It has also been suggested that LIMK inhibitors may be useful in treating glaucoma by promoting actin depolymerization in trabecular cells and lowering ocular tension. See International Application No. WO 04/047868. Current glaucoma therapies operate by different mechanisms. Prostaglandin F2a analogues (e.g., latanoprost) effect an intraocular pressure (IOP) independent increase in fluid outflow from the eye. Carbonic anhydrous inhibitors (e.g., acetazolamide), beta-blockers (e.g., timolol), sympathomimetics (e.g., pilocarpine), and alpha adrenergic receptor agonists (e.g., brimonidine) decrease aqueous humor production.

An enormous number of compounds, with a wide variety of chemotypes, have been reported as kinase inhibitors. For example, phenyl-substituted pyrimidine compounds have been disclosed that are reportedly useful as LIMK inhibitors. See International Application WO 2006/084017. Pyrrole[2,3-d]pyrimidine-based compounds have been disclosed as inhibitors of various different kinases. See, e.g., U.S. patent publication no. 2004/0058922; International Application WO 2007/125325; International Application WO 2007/125321; International Application WO 2006/046024; U.S. patent publication no. 2005/0130954; and U.S. patent publication no. 2006/0189638.

3. SUMMARY OF THE INVENTION

This invention is directed, in part, to compounds of the formula:

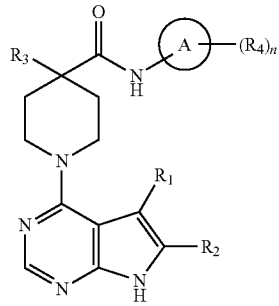

and pharmaceutically acceptable salts thereof, the substituents of which are defined herein. Particular compounds are potent inhibitors of LIMK2.

One embodiment of the invention encompasses pharmaceutical formations comprising compounds disclosed herein.

Another embodiment encompasses methods of using the compounds disclosed herein for the treatment, management and prevention of various diseases and disorders affected by LIMK2, including cancer, inflammatory diseases and disorders, and disease and disorders affecting vision (e.g., diseases and disorders of the eye), such as glaucoma, neurodegeneration and infection.

4. BRIEF DESCRIPTION OF THE FIGURE

FIG. 1 shows the effect of two compounds in the ocular hypertension assay described in the Examples below. Compound A is a compound of the invention, dosed at 3 μg per eye. The other compound, timolol, was dosed at 15 μg per eye. Data for the vehicle control is an average of eight experiments using different vehicles. Data for compound A is an average of eight experiments using different vehicles. Data for timolol is an average of two experiments obtained using a commercial formulation.

5. DETAILED DESCRIPTION

This invention is based, in part, on the discovery of novel compounds, which are inhibitors of LIM kinase 2 (LIMK2). LIMK2 inhibitors may be used to treat, manage and/or prevent a variety of diseases and disorders of the eye, such as glaucoma. See, e.g., U.S. patent application Ser. No. 12/188,515, filed Aug. 8, 2008. Preferred compounds of this invention are stable in solution, and may therefore be incorporated into liquid dosage forms such as eye drops. In addition, particular compounds are water soluble.

5.1. Definitions

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include, but are not limited to, anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "aryl-alkyl" means an aryl moiety bound to an alkyl moiety.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroalkylaryl" or "heteroalkyl-aryl" refers to a heteroalkyl moiety bound to an alkyl moiety.

Unless otherwise indicated, the term "heteroalkylheterocycle" or "heteroalkyl-heterocycle" refers to a heteroalkyl moiety bound to heterocycle moiety.

Unless otherwise indicated, the term "heteroaryl" means an aryl moiety wherein at least one of its carbon atoms has been replaced with a heteroatom (e.g., N, O or S). Examples include, but are not limited to, acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include, but are not limited to, benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moiety.

Unless otherwise indicated, the term "LIMK2 IC$_{50}$" is the IC$_{50}$ of a compound determined using the in vitro human LIM kinase 2 inhibition assay described in the Examples, below.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences*, 18$^{th}$ ed. (Mack Publishing, Easton Pa.: 1990) and *Remington: The Science and Practice of Pharmacy*, 19$^{th}$ ed. (Mack Publishing, Easton Pa.: 1995).

Unless otherwise indicated, a "potent LIMK2 inhibitor" is a compound that has a LIMK2 IC$_{50}$ of less than about 250 nM.

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or prevent its recurrence. A "prophylactically effective amount" of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, the term "stereoisomeric mixture" encompasses racemic mixtures as well as stereomerically enriched mixtures (e.g., R/S=30/70, 35/65, 40/60, 45/55, 55/45, 60/40, 65/35 and 70/30).

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Unless otherwise indicated, the term "substituted," when used to describe a chemical structure or moiety, refers to a derivative of that structure or moiety wherein one or more of its hydrogen atoms is substituted with a chemical moiety or functional group such as, but not limited to, alcohol, aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (e.g. —C(O)NH-alkyl-, -alkyl-NHC(O)alkyl), amidinyl (e.g., —C(NH)NH-alkyl-, —C(NR)NH$_2$), amine (primary, secondary and tertiary such as alkylamino, arylamino, arylalkylamino), aroyl, aryl, aryloxy, azo, carbamoyl (e.g., —NHC(O)O-alkyl-, —OC(O)NH-alkyl), carbamyl (e.g., CONH$_2$, CONH-alkyl, CONH-aryl, CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxo, phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (e.g., —NHCONH-alkyl-).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

5.2. Compounds

This invention encompasses compounds of the formula:

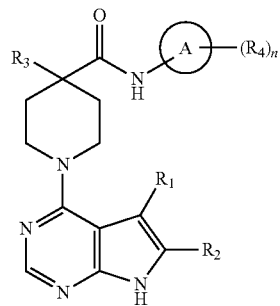

and pharmaceutically acceptable salt thereof, wherein: A is optionally substituted aryl or heterocycle; $R_1$ is hydrogen, halogen, cyano, or optionally substituted alkyl, heteroalkyl, aryl, or heterocycle; $R_2$ is hydrogen, halogen, cyano, or optionally substituted alkyl, heteroalkyl, aryl, or heterocycle; $R_3$ is $R_{3A}$, $OR_{3B}$, $N(R_{3B})_2$, $NC(O)R_{3B}$, $NC(O)OR_{3B}$, $NC(O)N(R_{3B})_2$, $SR_{3B}$, $SOR_{3B}$, or $SO_2R_{3B}$; each $R_{3A}$ is cyano, $C(O)R_{3C}$, $CO_2R_{3C}$, $CON(R_{3C})_2$, or optionally substituted alkyl, alkylaryl, alkylheterocycle, aryl, heteroalkyl, heteroalkylaryl, heteroalkylheterocycle, or heterocycle; each $R_{3B}$ is independently hydrogen, $C(O)R_{3C}$, $CO_2R_{3C}$, $CON(R_{3C})_2$, or optionally substituted alkyl, heteroalkyl, aryl, or heterocycle; each $R_{3C}$ is independently optionally substituted alkyl, aryl or heterocycle; each $R_4$ is independently hydrogen, halogen, $OR_{4B}$, $OC(O)R_{4B}$, $OC(O)N(R_{4B})_2$, $N(R_{4B})_2$, $NC(O)R_{4A}$, $NC(O)OR_{4A}$, $NC(O)N(R_{4A})$, $SR_{4B}$, $SOR_{4B}$, or $SO_2R_{4B}$, or optionally substituted alkyl, heteroalkyl, aryl, or heterocycle; each $R_{4B}$ is independently hydrogen or optionally substituted alkyl, heteroalkyl, aryl, or heterocycle; and n is 0-3.

In a particular embodiment, the compound is such that: 1) each $R_{4A}$ is independently hydrogen or optionally substituted alkyl or heteroalkyl; and 2) when $R_1$ and $R_2$ are both hydrogen and A is phenyl, $R_4$ is not halogen.

In one embodiment, A is optionally substituted phenyl. In another, A is optionally substituted heterocycle.

In one embodiment, $R_1$ is hydrogen, halogen, cyano, or optionally substituted lower alkyl. In a particular embodiment, $R_1$ is hydrogen. In another, $R_1$ is halogen (e.g., chloro). In another, $R_1$ is optionally substituted lower alkyl (e.g., methyl).

In one embodiment, $R_2$ is hydrogen, halogen, cyano, or optionally substituted lower alkyl. In a particular embodiment, $R_2$ is hydrogen. In another, $R_2$ is halogen (e.g., chloro). In another, $R_2$ is optionally substituted lower alkyl (e.g., methyl).

In one embodiment, $R_3$ is $R_{3A}$, $OR_{3B}$, or $N(R_{3B})_2$. In a particular embodiment, $R_3$ is $R_{3A}$ and $R_{3A}$ is optionally substituted alkyl, alkylheterocycle, heteroalkyl, or heterocycle. In a specific embodiment, $R_{3A}$ is optionally substituted alkyl. In another, $R_{3A}$ is optionally substituted alkylheterocycle. In another, $R_{3A}$ is optionally substituted heteroalkyl. In another, $R_{3A}$ is optionally substituted heterocycle. In a particular embodiment, $R_3$ is $OR_{3B}$ or $N(R_{3B})_2$, and $R_{3B}$ is hydrogen or optionally substituted alkyl or aryl. In a specific embodiment, $R_{3B}$ is hydrogen. In another, $R_{3B}$ is optionally substituted alkyl. In another, $R_{3B}$ is optionally substituted aryl.

In one embodiment, $R_4$ is halogen. In another, $R_4$ is $OC(O)N(R_{4A})_2$ and at least one $R_{4A}$ is, for example, lower alkyl (e.g., methyl).

Particular compounds of the invention are potent LIMK2 inhibitors. Certain compounds have a LIMK2 $IC_{50}$ of less than about 100, 75, 50, 25 or 10 nM.

5.3. Methods Of Synthesis

Compounds of the invention may be prepared by methods known in the art. See, e.g., U.S. patent publication nos. 2004/0058922 and 2005/0130954.

Pyrrolopyrimidines may be prepared by a variety of methods known in the art. See, e.g., West, *J. Org. Chem.* 26:4959 (1961); Aono et al., EP 0733633-B1. One approach is described in U.S. patent application Ser. No. 11/876,051, filed Oct. 22, 2007, and shown below in Scheme 1:

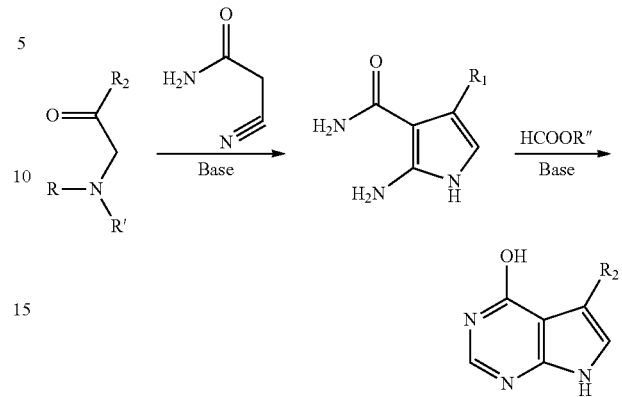

The resulting 4-hydroxy pyrrolo[2,3-d]pyrimidine compound is then converted to the corresponding 4-chloro compound (compound f in Scheme 2, below) using methods known in the art. See, e.g., West, *J. Org. Chem.* 26:4959 (1961). That compound is then used to prepare compounds of the invention, as shown below in Scheme 2:

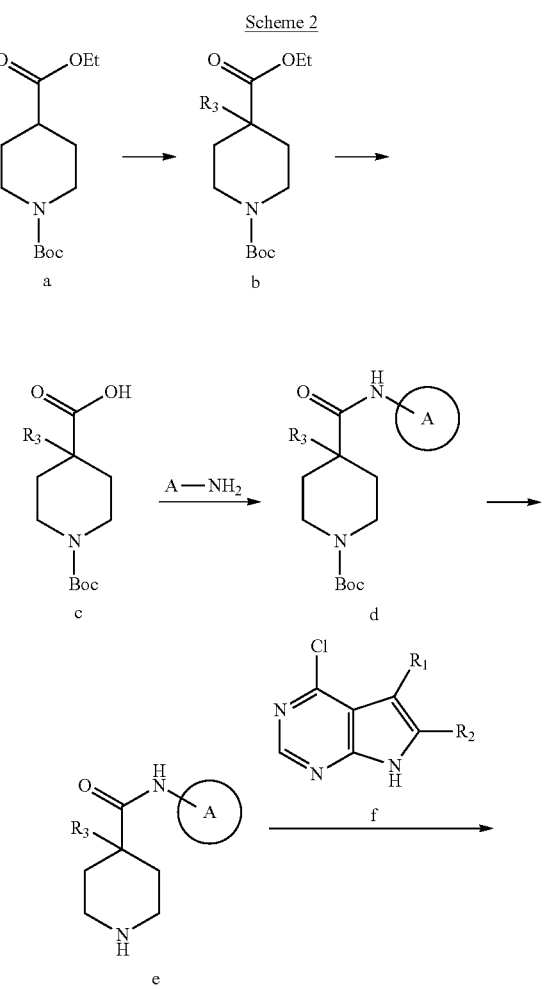

-continued

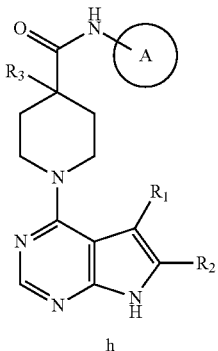

h

In the method represented in Scheme 2, commercially available 1-tert-butyl 4-ethyl piperidine-1,4-dicarboxylate (a) is alkylated with a suitable base (e.g., lithium diisopropyl amide) and an alklylating agent, (e.g., an alkyl bromide or chloride), to give compound b. Other compounds of formula b are commercially available. Saponification of compound b with a base such as LiOH or NaOH in aqueous solution gives carboxylic acid c, which can be coupled with amines of formula $NH_2A$ using suitable reagents (e.g., HATU with diisopropylethylamine in isopropyl acetate) to give amide d. Treatment of compound d with a suitable acid (e.g., HCl in MeOH or TFA in $CH_2Cl_2$) removes the Boc group to give amine e. Heating amine e and chloride f with a suitable base (e.g., diisopropylethylamine) in a suitable solvent (e.g., isopropanol, isobutanol) affords compound h. If desired, known methods can be used to transform that compound into various others encompassed by this invention.

5.4. Methods Of Use

This invention encompasses a method of inhibiting LIMK2, which comprises contacting LIMK2 with a potent LIMK2 inhibitor. Preferred potent LIMK2 inhibitors are compounds of the invention (i.e., compounds disclosed herein).

A particular embodiment encompasses a method of treating, managing or preventing an inflammatory disease or disorder in a patient, which comprises administering to the patient in need thereof a therapeutically or prophylactically effective amount of a compound of the invention.

Another embodiment encompasses a method of treating, managing or preventing cancer in a patient, which comprises administering to the patient in need thereof a therapeutically or prophylactically effective amount of a compound of the invention.

Another embodiment encompasses a method of lowering intraocular pressure in a patient, which comprises inhibiting LIMK2 activity or expression in a patient in need thereof. In one method, LIMK2 activity is inhibited by contacting the eye of the patient with a potent LIMK2 inhibitor. Particular potent LIMK2 inhibitors are disclosed herein. In another method, LIMK2 expression is inhibited by administering to the eye of the patient a compound (e.g., a siRNA) that inhibits the expression of LIMK2.

Another embodiment encompasses a method of treating, managing or preventing a disease or disorder affecting vision in a patient, which comprises inhibiting LIMK2 activity or expression in a patient in need thereof. In one method, LIMK2 activity is inhibited by contacting the eye of the patient with a potent LIMK2 inhibitor. Particular potent LIMK2 inhibitors are disclosed herein. Diseases and disorders affecting vision include glaucoma, neurodegenerative diseases, and infectious diseases.

5.5. Pharmaceutical Formulations

This invention encompasses pharmaceutical compositions comprising one or more compounds of the invention. Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), transdermal, topical and ophthalmic (e.g., topical, intravitreal) administration to a patient.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18$^{th}$ ed. (Mack Publishing, Easton Pa.: 1990).

5.5.1. Oral Dosage Forms

Pharmaceutical compositions of the invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See, e.g., *Remington's Pharmaceutical Sciences,* 18$^{th}$ ed. (Mack Publishing, Easton Pa.: 1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

5.5.2. Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5.5.3. Transdermal, Topical and Mucosal Dosage Forms

Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, 18$^{th}$ ed. (Mack Publishing, Easton Pa.: 1990); and *Introduction to Pharmaceutical Dosage Forms*, 4$^{th}$ ed. (Lea & Febiger, Philadelphia: 1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5.5.4. Ophthalmic Dosage Forms

Compounds of the invention can be delivered to the eye (e.g., topically) using aqueous solutions, aqueous suspensions, and ointments. As those skilled in the art are aware, the ophthalmic product must be sterile in its final container to prevent microbial contamination of the eye. Preservatives may be used to maintain sterility once the container has been opened. Ophthalmic formulations also require that the pH, buffer capacity, viscosity, and tonicity of the formulation be controlled. Preferred formulations have a pH of from about 6.5 to 8.5, and a buffer capacity of from about 0.01 to 0.1. Particular formations are isotonic. Particular formations have a viscosity of from about 25 to 50 cps.

Ingredients that may be used to provide safe vehicles that effectively deliver an active pharmaceutical ingredient (API) to its site of action are well known, but will vary depending on the physical and chemical characteristics of the API.

Appropriately buffered aqueous solutions may be used for the delivery of water soluble compounds. In solution compositions, polymeric ingredients are typically used to increase the composition's viscosity. Examples of suitable polymers include cellulosic polymers (e.g., hydroxypropyl methylcellulose, hydroxyethyl cellulose, ethylhydroxyethyl cellulose), synthetic polymers (e.g., carboxyvinyl polymers, polyvinyl alcohol), polysaccharides (e.g., xanthan gum, guar gum, and dextran), and mixtures thereof. See, e.g., U.S. Pat. Nos. 4,136, 173 and 7,244,440. Suspensions may also be used to deliver compounds. Polymeric ingredients are typically used in suspension compositions as physical stability aids, helping to keep the insoluble ingredients suspended or easily redispersible. Id.

Preservatives may be used to ensure the sterility of formations. Suitable preservatives include benzalkonium chloride, benzethonium chloride, chlorobutanol, phenylmercuric acetate, phenylmercuric nitrate, thimerosal, methylparaben, and propyl-parabens. And antioxidants may be used to ensure the stability of formations susceptible to oxidation. Suitable antioxidants include ethylenediaminetetraacetic acid, sodium bisulfite, sodium metabisulfite, and thiourea.

6. EXAMPLES

Aspects of this invention can be understood from the following examples, which do not limit its scope.

6.1. Example 1

Synthesis of 1-(5-chloro-7H-pyrrolo[2,3-d]pyrimidin-4-yl)-N-(3-(4-fluorophenoxy)phenyl)-4-methylpiperidine-4-carboxamide

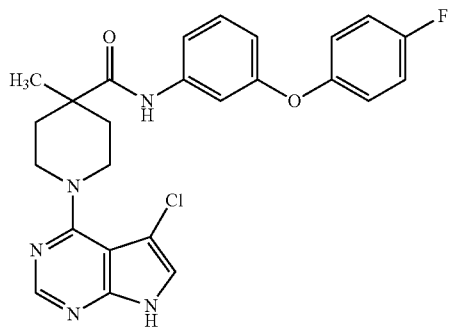 [SMILES: CC1(C(=O)Nc2cccc(Oc3ccc(F)cc3)c2)CCN(c2ncnc3[nH]cc(Cl)c23)CC1]

A. Preparation of tert-butyl 4-(3-(4-fluorophenoxy)phenylcarbamoyl)-4-methylpiperidine-1-carboxylate. 1-(tert-butoxycarbonyl)-4-methylpiperidine-4-carboxylic acid (243 mg, 1.0 mmol), 3-(4-fluorophenoxy)aniline (203 mg, 1.0 mmol), DCC (206 mg, 1.0 mmol), and HOAt (138 mg, 1.01 mmol) were combined in EtOAc (50 mL) and DMF (5 mL). The reaction mixture was heated at 80° C. for 20 hours. Most of the EtOAc was evaporated, resulting in precipitation of a solid, which was removed by filtration. The filtrate was diluted with EtOAc, washed with 1 N aq. HCl, water, and brine, dried, and concentrated under vacuum to give the title compound. MS (ES+) [M+H]$^+$=429.

B. Preparation of N-(3-(4-fluorophenoxy)phenyl)-4-methylpiperidine-4-carboxamide. tert-Butyl 4-(3-(4-fluorophenoxy)phenylcarbamoyl)-4-methylpiperidine-1-carboxylate from step A was treated with 4 N HCl in dioxane for 16 hours at room temperature. The product was isolated by filtration and washed with ether to afford the title compound (206 mg, 56% for two steps) as the hydrochloride salt. MS (ES+) [M+H]$^+$=329.

C. Preparation of 4,5-dichloro-7H-pyrrolo[2,3-d]pyrimidine. To a solution of 4-chloro-7H-pyrrolo[2,3-d]pyrimidine (154 mg, 1.0 mmol) in CH$_2$Cl$_2$ (6 mL) was added NCS (134 mg, 1.0 mmol). The reaction mixture was refluxed for 18 hours, filtered, and concentrated under vacuum to give the title compound, which was carried on crude. MS (ES+) [M+H]$^+$=189.

D. Preparation of 1-(5-chloro-7H-pyrrolo[2,3-d]pyrimidin-4-yl)-N-(3-(4-fluorophenoxy)phenyl)-4-methylpiperidine-4-carboxamide. N-(3-(4-Fluorophenoxy)phenyl)-4-methylpiperidine-4-carboxamide from step B (50 mg, 0.13 mmol), 4,5-dichloro-7H-pyrrolo[2,3-d]pyrimidine from step C (19 mg, 0.1 mmol), and triethylamine (0.04 mL, 0.3 mmol) were combined in isopropanol (1 mL) and heated at 130° C. for 30 minutes under microwave conditions. The product was isolated by prep HPLC to give the title compound.

$^1$H NMR (CD$_3$OD): δ 8.22 (s, 1H), 7.30-7.35 (m, 4H), 7.03-7.14 (m, 4H), 6.73-6.76 (m, 1H), 3.96-4.02 (m, 2H), 3.44-3.51 (m, 2H), 2.35-2.38 (m, 2H), 1.74-1.81 (m, 2H), 1.38 (s, 3H); MS (ES+) [M+H]$^+$=480.

6.2. Example 2

Synthesis of 1-(5-bromo-7H-pyrrolo[2,3-d]pyrimidin-4-yl)-N-(3-(4-fluorophenoxy)phenyl)-4-methylpiperidine-4-carboxamide

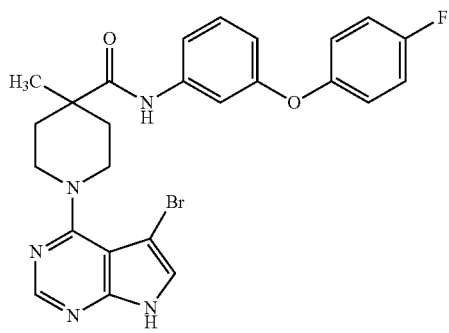 [SMILES: CC1(C(=O)Nc2cccc(Oc3ccc(F)cc3)c2)CCN(c2ncnc3[nH]cc(Br)c23)CC1]

A. Preparation of 5-bromo-4-chloro-7H-pyrrolo[2,3-d]pyrimidine. To a solution of 4-chloro-7H-pyrrolo[2,3-d]pyrimidine (1.2 g, 7.8 mmol) in CH$_2$Cl$_2$ (25 mL) was added N-bromoacetamide (1.2 g, 8.7 mmol) in CH$_2$Cl$_2$ (25 mL). The reaction mixture was refluxed for 40 minutes, then concentrated and washed with cold water. The crude material was recrystallized from a minimal amount of isopropanol and dried under vacuum to give the title compound (82%) as light-gray solid. MS (ES+) [M+H]$^+$=232.

B. Preparation of 1-(5-bromo-7H-pyrrolo[2,3-d]pyrimidin-4-yl)-N-(3-(4-fluorophenoxy)phenyl)-4-methylpiperidine-4-carboxamide. To a solution of N-(3-(4-fluorophenoxy)phenyl)-4-methylpiperidine-4-carboxamide from example 1, step B, (36 mg, 0.1 mmol) in isopropanol (1 mL), was added to 5-bromo-4-chloro-7H-pyrrolo[2,3-c]pyrimidine from step A (24 mg, 0.1 mmol) and triethylamine (0.04 mL, 0.3 mmol). The reaction mixture was heated at 100° C. for 10 minutes under microwave condition, and then concentrated under vacuum. The product was isolated by prep HPLC to give the title compound.

$^1$H NMR (CD$_3$OD): δ 8.21 (s, 1H), 7.22-7.35 (m, 4H), 6.98-7.17 (m, 4H), 6.72-6.77 (m, 1H), 3.84-3.95 (m, 2H), 3.32-3.51 (m, 2H), 2.30-2.40 (m, 2H), 1.72-1.85 (m, 2H), 1.38 (s, 3H); MS (ES+) [M+H]$^+$=525.

6.3. Example 3

Synthesis of N-(3-(4-fluorophenoxy)phenyl)-4-methyl-1-(7H-pyrrolo[2,3-d]pyrimidin-4-yl)piperidine-4-carboxamide

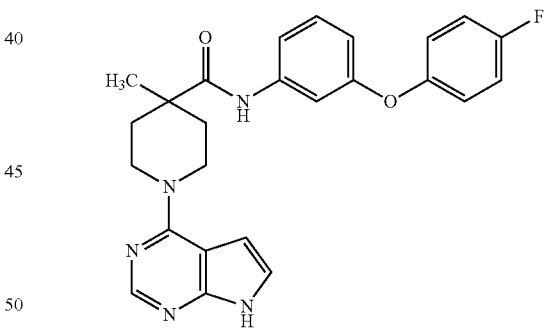

To a solution of N-(3-(4-fluorophenoxy)phenyl)-4-methylpiperidine-4-carboxamide from example 1, step B, (20 mg, 0.05 mmol) in isopropanol (1 mL), was added 4-chloro-7H-pyrrolo[2,3-d]pyrimidine (15 mg, 0.1 mmol) and triethylamine (0.04 mL, 0.3 mmol). The reaction mixture was heated at 180° C. for 30 minutes under microwave conditions, and then concentrated under vacuum. The product was isolated by prep HPLC to give the title compound.

$^1$H NMR (CD$_3$OD): δ 8.01 (s, 1H), 7.18-7.23 (m, 3H), 6.91-7.16 (m, 5H), 6.65-6.68 (d, 1H), 6.51-6.53 (d, 1H), 4.12-4.25 (m, 2H), 3.351-3.62 (m, 2H), 2.13-2.28 (m, 2H), 1.50-1.60 (m, 2H), 1.25 (s, 3H); MS (ES+) [M+H]$^+$=447.

6.4. Example 4

Synthesis of N-(3-tert-butylphenyl)-1-(5-methyl-7H-pyrrolo[2,3-d]pyrimidin-4-yl)-4-phenylpiperidine-4-carboxamide

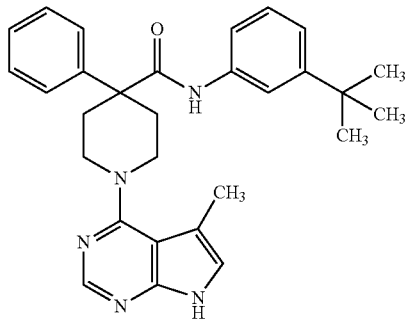 [SMILES: Cc1c[nH]c2ncnc(N3CCC(C(=O)Nc4cccc(C(C)(C)C)c4)(c4ccccc4)CC3)c12]

A. Preparation of 4-phenylpiperidine-4-carboxylic acid. 1-(tert-Butoxycarbonyl)-4-phenylpiperidine-4-carboxylic acid (1.0 g, 3.3 mmol) was treated with 4 N HCl in dioxane (20 mL) for 2 hours at room temperature. The product was isolated by filtration to provide the title compound (0.74 g, 93%) as a white solid. MS (ES+) [M+H]$^+$=206.

B. Preparation of 1-(5-methyl-4,7-dihydro-3H-pyrrolo[2,3-d]pyrimidin-4-yl)-4-phenylpiperidine-4-carboxylic acid. To a solution of 4-phenylpiperidine-4-carboxylic acid from step A (0.74 g, 3.1 mmol) in isopropanol (10 mL), was added 4-chloro-5-methyl-7H-pyrrolo[2,3-d]pyrimidine (0.52 g, 3.1 mmol) and triethylamine (1.0 mL, 9.8 mmol). The reaction mixture was heated at 180° C. for 180 minutes under microwave condition, and then concentrated under vacuum. The residue was dissolved in ice water and neutralized to pH 4 by addition of 1 N aq. HCl. The product was isolated by filtration and dried under vacuum for 3 hours at 65° C. to give the title compound (62%) as a brown solid. MS (ES+) [M+H]$^+$=336.

C. Preparation of N-(3-tert-butylphenyl)-1-(5-methyl-7H-pyrrolo[2,3-d]pyrimidin-4-yl)-4-phenylpiperidine-4-carboxamide. To a solution of 1-(5-methyl-4,7-dihydro-3H-pyrrolo[2,3-d]pyrimidin-4-yl)-4-phenylpiperidine-4-carboxylic acid from step B (33 mg, 0.1 mmol) in DMF (2 mL) was added 3-tert-butylaniline (15 mg, 1.0 mmol), BOP (50 mg, 0.11 mmol) and triethylamine (0.04 mL, 0.3 mmol). The reaction mixture was stirred at room temperature for 20 hours, and the amide product was isolated by prep HPLC to give the title compound.

$^1$H NMR (CD$_3$OD): δ 8.20 (s, 1H), 7.16-7.57 (m, 9H), 7.01 (s, 1H), 3.90-3.94 (d, 2H), 3.45-3.52 (t, 2H), 2.73-2.78 (d, 2H), 2.46 (s, 3H), 2.28-2.35 (t, 2H), 1.30 (s, 9H); MS (ES+) [M+H]$^+$=468.

6.5. Example 5

Synthesis of 4-allyl-N-(3-chlorophenyl)-1-(5-methyl-7H-pyrrolo[2,3-d]pyrimidin-4-yl)piperidine-4-carboxamide

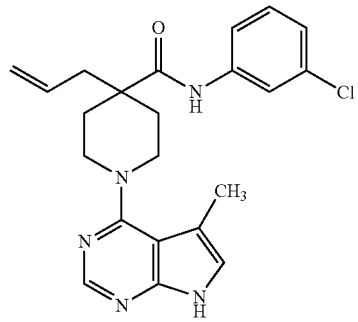 [SMILES: C=CCC1(C(=O)Nc2cccc(Cl)c2)CCN(c2ncnc3[nH]cc(C)c23)CC1]

A. Preparation of tert-butyl 4-allyl-4-(3-chlorophenylcarbamoyl)piperidine-1-carboxylate. Under an atmosphere of N$_2$, 4-allyl-1-(tert-butoxycarbonyl)piperidine-4-carboxylic acid (0.158 g, 0.586 mmol), pyridine (0.189 mL, 2.34 mmol), and DMF (3 drops) were dissolved in CH$_2$Cl$_2$ (10 mL) and cooled in an ice bath. To the cooled solution, oxalyl chloride (0.056 mL, 0.645 mmol) was added dropwise. The reaction was stirred for 40 min, after which time 3-chloroaniline (0.061 mL, 0.586 mmol) was added. The reaction was removed from the ice bath and stirred at room temperature overnight. The crude reaction was washed with 1 N aq. HCl and brine, dried over MgSO$_4$, and concentrated under vacuum. The residue was purified by silica gel chromatography (ethyl acetate/hexanes gradient) to give the title compound in 51% yield. MS (ES+) [M+H]$^+$=379.

B. Preparation of 4-allyl-N-(3-chlorophenyl)piperidine-4-carboxamide. To a solution of tert-butyl 4-allyl-4-(3-chlorophenylcarbamoyl)piperidine-1-carboxylate from step A (0.172 g, 0.453 mmol) in MeOH (10 mL) was added 4 M HCl in dioxane (0.340 mL, 1.36 mmol). The reaction was heated at 50° C. for 30 min, and then concentrated under vacuum, re-dissolved in MeOH and re-concentrated twice to give the title compound as the hydrochloride salt. MS (ES+) [M+H]$^+$ 279.

C. Preparation of 4-allyl-N-(3-chlorophenyl)-1-(5-methyl-7H-pyrrolo[2,3-d]pyrimidin-4-yl)piperidine-4-carboxamide. 4-Allyl-N-(3-chlorophenyl)piperidine-4-carboxamide from step B (0.142 g, 0.453 mmol), 4-chloro-5-methyl-7H-pyrrolo[2,3-d]pyrimidine (0.075 g, 0.453 mmol), N,N-diisopropylethylamine (0.236 mL, 1.35 mmol), and isopropanol (5 mL) were combined and heated at 120° C. overnight in a pressure vessel. The crude reaction was dissolved in CH$_2$Cl$_2$, washed with H$_2$O and brine, dried over MgSO$_4$, and concentrated under vacuum. The residue was purified by silica gel chromatography (MeOH:CH$_2$Cl$_2$ gradient) to give the title compound in 61% yield.

$^1$H NMR (400 MHz, CD$_3$OD) δ ppm 8.19 (s, 1H), 7.73 (s, 1H), 7.48 (d, J=8 Hz, 1H), 7.32 (t, J=8, 16 Hz, 1H), 7.14 (d, J=8 Hz, 1H), 7.00 (s, 1H), 5.78-5.88 (m, 1H), 5.11-5.16 (m, 2H), 3.91 (d, J=13.6 Hz, 2H), 3.24-3.30 (m, 2H), 2.50 (d, J=7.6 Hz, 2H), 2.45 (s, 3H), 2.41 (d, J=13.6 Hz, 2H), 1.80-1.86 (m, 2H); MS (ES+) [M+H]$^+$=410.

6.6. Example 6

Synthesis of N-(3-methoxyphenyl)-4-methyl-1-(5-methyl-7H-pyrrolo[2,3-d]pyrimidin-4-yl)piperidine-4-carboxamide

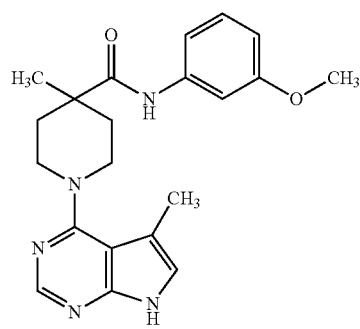 [SMILES: COc1cccc(NC(=O)C2(C)CCN(c3ncnc4[nH]cc(C)c34)CC2)c1]

A. Preparation of 4-methylpiperidine 4-carboxylic acid. 1-(tert-Butoxycarbonyl)-4-methylpiperidine-4-carboxylic acid (0.500 g, 2.06 mmol) was treated with 4 M HCl in dioxane (10 mL) for 2 hours at room temperature to afford the title compound (0.294 g, 100%) as the hydrochloride salt. MS (ES+) [M+H]$^+$=144.0.

B. Preparation of 4-methyl-1-(5-methyl-7H-pyrrolo[2,3-d]pyrimidin-4-yl)-piperidine-4-carboxylic acid. To a solution of 4-chloro-5-methyl-7H-pyrrolo[2,3-d]pyrimidine (0.274 g, 1.64 mmol) in isopropanol (10 mL) were added 4-methylpiperidine 4-carboxylic acid hydrochloric acid from step A (0.294 g, 1.64 mmol) and triethylamine (0.654 mL, 4.92 mmol). The reaction was heated to 180° C. for 1 hour under microwave conditions, concentrated, taken up with ice water, and neutralized to pH 3 with 6 N aq. HCl to precipitate the product. The product was collected by filtration and dried under vacuum overnight to give the title compound (0.42 g, 75%) as a gray solid. MS (ES+) [M+H]$^+$275.2.

C. Preparation of N-(3-methoxyphenyl)-4-methyl-1-(5-methyl-7H-pyrrolo[2,3-d]pyrimidin-4-yl)piperidine-4-carboxamide. To a solution of 4-methyl-1-(5-methyl-7H-pyrrolo[2,3-d]pyrimidin-4-yl)-piperidine-4-carboxylic acid from step B (0.020 g, 0.073 mmol) in DMF (1 mL) were added BOP reagent (0.065 g, 0.15 mmol), triethylamine (0.019 mL, 0.15 mmol), and 3-methoxyaniline (0.012 mL, 0.11 mmol). The reaction was stirred overnight, and then concentrated under vacuum. The residue was purified by prep HPLC to give the title compound (0.091 g, 33%).

$^1$H NMR (CD$_3$OD): δ 8.07 (1H, bs), 7.00-7.17 (3H, m), 6.89 (1H, s), 6.58-6.61 (1H, m), 3.62-3.72 (5H, m), 3.22-3.34 (2H, m), 2.12-2.33 (5H, m), 1.62-1.71 (2H, m), 1.29 (3H, s); MS (ES+) [M+H]$^+$=380.1.

6.7. Example 7

Synthesis of 4-methyl-1-(5-methyl-7H-pyrrolo[2,3-d]pyrimidin-4-yl)-N-p-tolylpiperidine-4-carboxamide

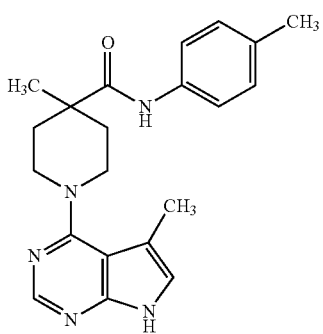 [SMILES: Cc1ccc(NC(=O)C2(C)CCN(c3ncnc4[nH]cc(C)c34)CC2)cc1]

To a solution of 4-methyl-1-(5-methyl-7H-pyrrolo[2,3-c]pyrimidin-4yl)-piperidine-4-carboxylic acid from example 6, step B, (0.020 g, 0.073 mmol) in DMF (1 mL) were added BOP reagent (0.065 g, 0.15 mmol), triethylamine (0.019 mL, 0.15 mmol), and 4-methylaniline (0.012 mL, 0.11 mmol). The reaction was stirred overnight and concentrated under vacuum. The residue was purified by prep HPLC to give the title compound (0.0133 g, 50%).

$^1$H NMR (CD$_3$OD): δ 8.07 (1H, bs), 7.31 (2H, J=8.4 Hz, d), 7.04 (2H, J=8.4 Hz, d), 6.89 (1H, s), 3.68-3.73 (2H, m), 3.21-3.44 (2H, m), 2.21-2.33 (8H, m), 1.62-1.71 (2H, m), 1.29 (3H, s); MS (ES+) [M+H]$^+$=364.2.

6.8. Example 8

Synthesis of N-(3-(isopropylcarbamoyl)phenyl)-4-methyl-1-(5-methyl-7H-pyrrolo[2,3-d]pyrimidin-4-yl)piperidine-4-carboxamide

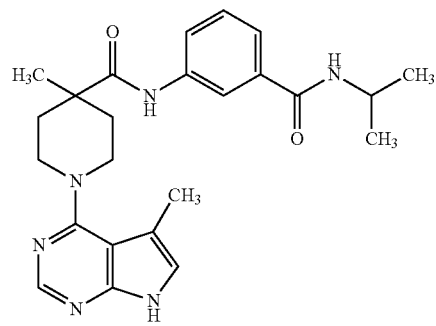 [SMILES: Cc1c[nH]c2ncnc(N3CCC(C)(C(=O)Nc4cccc(C(=O)NC(C)C)c4)CC3)c12]

To a solution of 4-methyl-1-(5-methyl-7H-pyrrolo[2,3-c]pyrimidin-4yl)-piperidine-4-carboxylic acid from example 6, step B, (0.030 g, 0.11 mmol) in DMF (1 mL) were added HATU (0.042 g, 0.11 mmol), triethylamine (0.028 mL, 0.22 mmol) and 3-amino-N-isopropyl-benzamide (0.029 mg, 0.17 mmol). The reaction was stirred at 50° C. for 48 hours and concentrated under vacuum. The residue was purified by prep HPLC to give the title compound (0.023 g, 48%).

$^1$H NMR (CD$_3$OD): δ 8.19 (1H, s), 7.99 (1H, m), 7.7-7.72 (1H, m), 7.56-7.58 (1H, m), 7.41-7.43 (1H, J=8 Hz and 15.6 Hz, dd), 7.00 (1H, J=0.8 Hz, d), 4.20-4.23 (1H, m), 3.79-3.85 (2H, m), 3.36-3.46 (2H, m), 2.38-2.44 (5H, m), 1.76-1.83 (2H, m), 1.42 (3H, s), 1.268 (6H, J=6.8 Hz, d); MS (ES+) [M+H]$^+$435.

6.9. Example 9

Synthesis of N-(3-tert-butylphenyl)-4-methyl-1-(5-methyl-7H-pyrrolo[2,3-d]pyrimidin-4-yl)piperidine-4-carboxamide

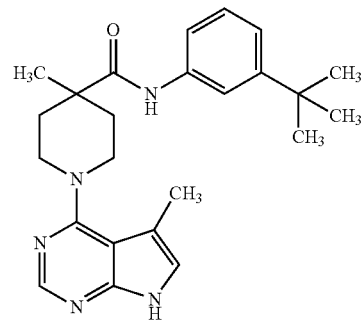 [SMILES: Cc1c[nH]c2ncnc(N3CCC(C)(C(=O)Nc4cccc(C(C)(C)C)c4)CC3)c12]

A. Preparation of tert-Butyl 4-(3-tert-butylphenylcarbamoyl)-4-methylpiperidine-1-carboxylate. To a solution of 1-(tert-butoxycarbonyl)-4-methylpiperidine-4-carboxylic acid (0.30 g, 1.2 mmol), DMF (20 drops), and pyridine (0.38 g, 4.8 mmol) in dichloroethane (10 mL) was added oxalyl chloride (0.15 g, 1.2 mmol). The mixture was stirred for 40 minutes, and 3-tert-butylaniline was added. The mixture was stirred for 1 hour, diluted with dichloromethane, washed twice each with sat. aq. NaHCO$_3$ and 1.0 N aq. HCl, dried over MgSO$_4$, and concentrated. Silica gel chromatography (0-2% MeOH:CH$_2$Cl$_2$) gave the title compound in 61% yield. MS (ES+) [M+H]$^+$375.

B. Preparation of N-(3-tert-butylphenyl)-4-methylpiperidine-4-carboxamide. tert-Butyl 4-(3-tert-butylphenylcarbamoyl)-4-methylpiperidine-1-carboxylate from step A (0.4 g, 1.07 mmol) was treated with HCl (4.0 N in dioxane, 1.3 mL, 5.34 mmol) in methanol (5.0 mL) at 50° C. for 30 minutes. The mixture was concentrated to give the title compound as the hydrochloride salt in quantitative yield. MS (ES+) [M+H]$^+$275.

C. N-(3-tert-butylphenyl)-4-methyl-1-(5-methyl-7H-pyrrolo[2,3-d]pyrimidin-4-yl)piperidine-4-carboxamide. N-(3-tert-Butylphenyl)-4-methylpiperidine-4-carboxamide from step B (0.33 g, 1.07 mmol), 4-chloro-5-methyl-7H-pyrrolo[2,3-d]pyrimidine (0.18 g, 1.07 mmol), N,N-diisopropylethylamine (0.69 g. 5.34 mmol), and isopropanol (7 mL) were combined in a pressure rated sealed tube and heated at 100° C. for 18 hours. The mixture was concentrated and taken up in dichloromethane from which a precipitate (0.18 g) was collected. The solution was chromatographed (SiO$_2$, 0-2% MeOH:CH$_2$Cl$_2$), and the columned material (0.15 g) was combined with the precipitate and dissolved in methanol (15 mL) at 60° C. Water was added (5.0 mL), and the mixture was cooled. The resultant precipitate was filtered, washed with water, and dried to give the title compound in 50% yield.
$^1$H NMR (400 MHz, DMSO-d$_6$) δ ppm 11.51 (s, 1H), 9.31 (s, 1H), 8.19 (s, 1H), 7.62 (s, 1H), 7.59 (d, J=8.0 Hz, 1H), 7.22 (t, J=8 Hz and 16 Hz, 1H), 7.08 (d, J=8.0 Hz, 1H), 3.63-3.68 (m, 2H), 3.28-3.33 (m, 2H), 2.36 (s, 3H), 2.25-2.29 (m, 2H), 1.63-1.68 (m, 2H), 1.31 (s, 3H), 1.27 (S, 9H); MS (ES+) [M+H]$^+$406.

6.10. Example 10

Synthesis of 4-methyl-1-(5-methyl-7H-pyrrolo[2,3-d]pyrimidin-4-yl)-N-(3-(oxazol-5-yl)phenyl)piperidine-4-carboxamide

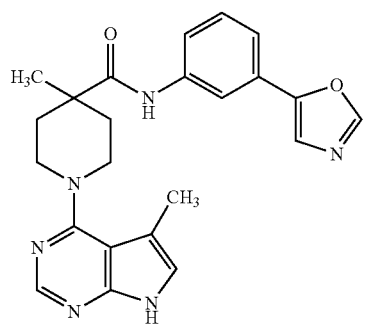 [SMILES: Cc1c[nH]c2ncnc(N3CCC(C)(C(=O)Nc4cccc(-c5cnco5)c4)CC3)c12]

A. Preparation of tert-butyl 4-methyl-4-(3-(oxazol-5-yl)phenylcarbamoyl)piperidine-1-carboxylate. To a solution of 1-(tert-butoxycarbonyl)-4-methylpiperidine-4-carboxylic acid (61.3 mg, 0.252 mmol) and pyridine (79.7 mg, 0.08 mL, 1.01 mmol) in 1,2-dichloroethane (2 mL) at 0° C. was added DMF (1-2 drops) followed by oxalyl chloride (31.9 mg, 0.022 mL, 0.252 mmol). The reaction was stirred for 0.5 hour, and 3-(oxazol-5-yl)aniline (40.4 mg, 0.252 mmol) was added. The reaction was allowed to stir for another 1.5 hours. The mixture was diluted with ethyl acetate (10 mL), and the organics were washed with 0.1 N HCl (2×10 mL), brine (4 mL), dried over MgSO$_4$, filtered, and concentrated to give the title compound, which was used in the next step without further purification. MS (ES+) [M+H]$^+$386.2.

B. Preparation of 4-methyl-N-(3-(oxazol-5-yl)phenyl)piperidine-4-carboxamide. To a solution of tert-butyl 4-methyl-4-(3-(oxazol-5-yl)phenylcarbamoyl)piperidine-1-carboxylate from step A (77.7 mg, 0.202 mmol) in methanol (3 mL) was added HCl (4.0 N in dioxane, 0.4 mL, 1.6 mmol). The reaction was stirred for 15 hours and then concentrated to dryness to give the title compound as the hydrochloride salt. MS (ES+) [M+H]$^+$286.2.

C. Preparation of 4-methyl-1-(5-methyl-7H-pyrrolo[2,3-d]pyrimidin-4-yl)-N-(3-(oxazol-5-yl)phenyl)piperidine-4-carboxamide. A pressure vessel was charged with a solution of 4-methyl-N-(3-(oxazol-5-yl)phenyl)piperidine-4-carboxamide hydrochloride from step B (51.9 mg, 0.17 mmol) and isopropanol (3 mL), and to this solution was added 4-chloro-5-methyl-7H-pyrrolo[2,3-d]pyrimidine (55.0 mg, 0.329 mmol) and N,N-diisopropylethylamine (297.9 mg, 0.40 mL, 2.31 mmol). The vessel was sealed, and the reaction was heated to 105° C. for 15 hours. The reaction was worked up by normal means, and the residue was purified by prep HPLC to afford the title compound as an off-white solid.
$^1$H NMR (400 MHz) δ ppm 8.27 (s, 1H), 8.18 (s, 1H), 8.03 (t, J=1.77 Hz, 1H), 7.58 (ddd, J=8.08, 2.02, 1.01 Hz, 1H), 7.52 (s, 1H), 7.50 (dt, J=8.08, 1.26 Hz, 1H), 7.43 (t, J=7.83 Hz, 1H), 7.00 (app. d, J=0.76 Hz, 1H), 3.78-3.86 (m, 2H), 3.38-3.46 (m, 2H), 2.44 (d, J=0.76 Hz, 3H), 2.36-2.44 (m, 2H), 1.79 (ddd, J=13.39, 9.85, 3.54 Hz, 2H), 1.42 (s, 3H); MS (ES+) [M+H]$^+$417.2.

6.11. Example 11

Synthesis of 4-methyl-1-(5-methyl-7H-pyrrolo[2,3-d]pyrimidin-4-yl)-N-(3-sulfamoylphenyl)piperidine-4-carboxamide

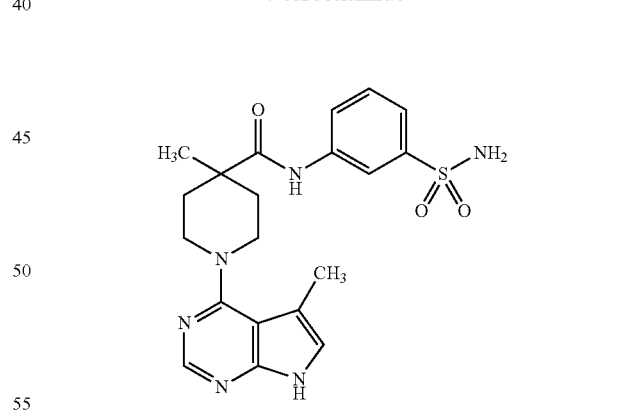

A. Preparation of tert-butyl 4-methyl-4-(3-sulfamoylphenylcarbamoyl)piperidine-1-carboxylate. To a solution of 1-(tert-butoxycarbonyl)-4-methylpiperidine-4-carboxylic acid (60 mg, 0.25 mmol) in dichloroethane (2.0 mL) were added DMF (2 drops) and pyridine (78 mg, 0.99 mmol), followed by oxalyl chloride (31 mg, 0.25 mmol). The mixture was stirred for 40 minutes, and 3-amino-benzenesulfonamide was added. The mixture was heated at 50° C. for 3 hours, and the mixture was cooled, diluted with dichloromethane, washed twice each with sat. aq. NaHCO$_3$ and 1.0 N aq. HCl, dried over MgSO$_4$, and concentrated. Silica gel chromatography (2-5% MeOH:CH$_2$Cl$_2$) gave the title compound in 40% yield. MS (ES+) [M+H]$^+$=398.

B. Preparation of 4-methyl-N-(3-sulfamoylphenyl)piperidine-4-carboxamide. tert-Butyl 4-methyl-4-(3-sulfamoylphenylcarbamoyl)piperidine-1-carboxylate from step A (39 mg, 0.098 mmol) was treated with HCl (4.0 N in dioxane, 98 μL, 0.39 mmol) in methanol (1.0 mL) at 50° C. for 45 minutes. The mixture was concentrated to give the title compound as the hydrochloride salt in quantitative yield. MS (ES+) [M+H]$^+$=298.

C. Preparation of 4-methyl-1-(5-methyl-7H-pyrrolo[2,3-d]pyrimidin-4-yl)-N-(3-sulfamoylphenyl)piperidine-4-carboxamide. 4-Methyl-N-(3-sulfamoylphenyl)piperidine-4-carboxamide from step B (33 mg, 0.098 mmol), 4-chloro-5-methyl-7H-pyrrolo[2,3-d]pyrimidine (16 mg, 0.098 mmol), N,N-diisopropylethylamine (51 mg, 0.39 mmol), and isopropanol (1.0 mL) were combined in a pressure rated sealed tube and heated at 105° C. for 18 hours. The mixture was concentrated, and the residue was purified by preparative HPLC to give the title compound in 21% yield.

$^1$H NMR (400 MHz, DMSO-d$_6$) δ ppm 11.52 (s, 1H), 9.72 (s, 1H), 8.24 (s, 1H), 8.19 (s, 1H), 7.87-7.90 (m, 1H), 7.50-7.52 (m, 2H), 7.35 (s, 2H), 7.06 (s, 1H), 4.09-4.13 (m, 1H), 3.66-3.40 (m, 2H), 3.25-3.31 (m, 2H), 3.18 (d, J=4 Hz, 2H), 2.36 (s, 3H), 2.27-2.30 (m, 2H), 1.64-1.70 (m, 2H), 1.32 (s, 3H); MS (ES+) [M+H]$^+$=429.

6.12. Example 12

Synthesis of N-(3-(1H-tetrazol-5-yl)phenyl)-4-methyl-1-(5-methyl-7H-pyrrolo[2,3-d]pyrimidin-4-yl)piperidine-4-carboxamide

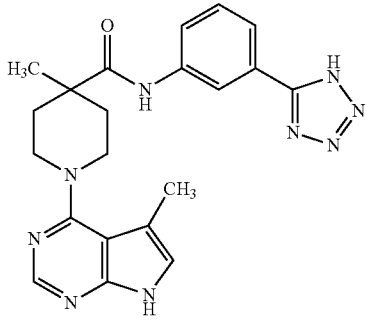 [SMILES: Cc1c[nH]c2ncnc(N3CCC(C)(C(=O)Nc4cccc(-c5nnn[nH]5)c4)CC3)c12]

A. Preparation of tert-butyl 4-(3-(1H-tetrazol-5-yl) phenylcarbamoyl)-4-methylpiperidine-1-carboxylate. To a solution of 1-(tert-butoxycarbonyl)-4-methylpiperidine-4-carboxylic acid (100 mg, 0.41 mmol) in dichloroethane (2.0 mL) were added DMF (2 drops) and pyridine (0.13 g, 1.6 mmol), followed by oxalyl chloride (57 mg, 0.45 mmol). The mixture was stirred for 40 minutes, and 3-(1H-tetrazol-5-yl)-phenylamine was added. The mixture was stirred for 2 hours, and a pink precipitate formed. The mixture was filtered, and the filtrate was washed with 1.0 N aq. HCl and brine, dried over MgSO$_4$, and concentrated to give the title compound in 70% yield. MS (ES+) [M+H]$^+$=387.

B. Preparation of N-(3-(1H-tetrazol-5-yl)phenyl)-4-methylpiperidine-4-carboxamide. tert-Butyl 4-(3-(1H-tetrazol-5-yl)phenylcarbamoyl)-4-methylpiperidine-1-carboxylate from step A (0.11 g, 0.29 mmol) was treated with HCl (4.0 N in dioxane, 0.36 mL, 1.45 mmol) in methanol (2.0 mL) and heated at 50° C. for 30 minutes. The mixture was concentrated to give the title compound as the hydrochloride salt in quantitative yield. MS (ES+) [M+H]$^+$=287.

C. Preparation of N-(3-(1H-tetrazol-5-yl)phenyl)-4-methyl-1-(5-methyl-7H-pyrrolo[2,3-d]pyrimidin-4-yl)piperidine-4-carboxamide. N-(3-(1H-tetrazol-5-yl)phenyl)-4-methylpiperidine-4-carboxamide from step B (93 mg, 0.29 mmol), 4-chloro-5-methyl-7H-pyrrolo[2,3-d]pyrimidine (49 mg, 0.29 mmol), N,N-diisopropylethylamine (0.19 g. 1.45 mmol), isopropanol (4.0 mL), and DMSO (0.5 mL) were combined in a pressure rated sealed tube and heated at 105° C. for 18 hours. The mixture was concentrated, and the residue was purified by preparative HPLC to give the title compound in 4.3% yield.

$^1$H NMR (400 MHz, DMSO-d$_6$) δ ppm 11.5 (s, 1H), 9.56 (s, 1H), 8.31 (s, 1H), 8.19 (s, 1H), 7.77 (d, J=8 Hz, 1H), 7.69 (d, J=8 Hz, 1H), 7.40 (t, J=8 and 16 Hz, 1H), 7.05 (s, 1H), 3.64-3.72 (m, 2H), 2.37 (s, 3H), 2.29-2.33 (m, 2H), 1.91 (s, 2H), 1.64-1.70 (m, 2H), 1.34 (s, 3H); MS (ES+) [M+H]$^+$=418.

6.13. Example 13

Synthesis of 3-(4-methyl-1-(5-methyl-7H-pyrrolo[2,3-d]pyrimidin-4-yl)piperidine-4-carboxamido)phenyl dimethylcarbamate

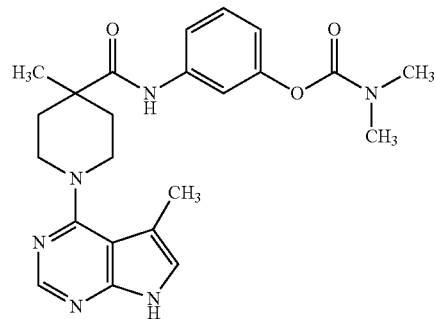 [SMILES: Cc1c[nH]c2ncnc(N3CCC(C)(C(=O)Nc4cccc(OC(=O)N(C)C)c4)CC3)c12]

A. Preparation of tert-butyl 4-(3-(dimethylcarbamoyloxy)phenylcarbamoyl)-4-methylpiperidine-1-carboxylate. 1-(tert-Butoxycarbonyl)-4-methylpiperidine-4-carboxylic acid (67 mg, 0.28 mmol), EDC (64 mg, 0.33 mmol), HOBT (45 mg, 0.33 mmol) and dichloroethane (2.0 mL) were combined in a pressure rated sealed tube and stirred for 45 min. 3-Aminophenyl dimethylcarbamate (50 mg, 0.28 mmol) was added, and the mixture was heated at 85° C. for 18 hours. The mixture was concentrated and chromatographed (SiO$_2$, 0-2% MeOH:CH$_2$Cl$_2$) to give the title compound in 50% yield. MS (ES+) [M+H]$^+$=406.

B. Preparation of 3-(4-methylpiperidine-4-carboxamido) phenyl dimethylcarbamate. tert-Butyl 4-(3-(dimethylcarbamoyloxy)phenylcarbamoyl)-4-methylpiperidine-1-carboxylate from step A (56 mgs, 0.138 mmol) was treated with HCl (4.0 N in dioxane, 0.17 mL, 0.69 mmol) in methanol (2.0 mL) at 40° C. for 3 hours. The mixture was concentrated to give the title compound as the hydrochloride salt in quantitative yield. MS (ES+) [M+H]$^+$=306.

C. Preparation of 3-(4-methyl-1-(5-methyl-7H-pyrrolo[2,3-d]pyrimidin-4-yl)piperidine-4-carboxamido)phenyl dimethylcarbamate. 3-(4-methylpiperidine-4-carboxamido)phenyl dimethylcarbamate from step B (47 mg, 0.14 mmol) 4-chloro-5-methyl-7H-pyrrolo[2,3-d]pyrimidine (23 mg, 0.138 mmol), N,N-diisopropylethylamine (54 mg, 0.41 mmol), and isopropanol (1.0 mL) were combined in a pressure rated sealed tube and heated at 100° C. for 18 hours. The mixture was concentrated, and the residue was purified by preparative HPLC to give the title compound in 53% yield.

$^1$H NMR (400 MHz, CD$_3$OD) δ ppm 8.18 (s, 1H), 7.50 (s, 1H), 7.42-7.44 (d, J=8 Hz, 1H), 7.34 (t, J=8 and 16 Hz, 1H), 7.0 (s, 1H), 6.87-6.89 (m, 1H), 3.79-3.85 (m, 2H), 3.37-3.44 (m, 2H), 3.14 (s, 1H), 3.01 (s, 3H), 2.44 (s, 3H), 2.36-2.40 (m, 2H), 1.75-1.81 (m, 2H), 1.40 (s, 3H); MS (ES+) [M+H]$^+$437.

6.14. Example 14

Synthesis of 3-(4-benzyl-1-(5-methyl-7H-pyrrolo[2,3-d]pyrimidin-4-yl)piperidine-4-carboxamido)phenyl dimethylcarbamate

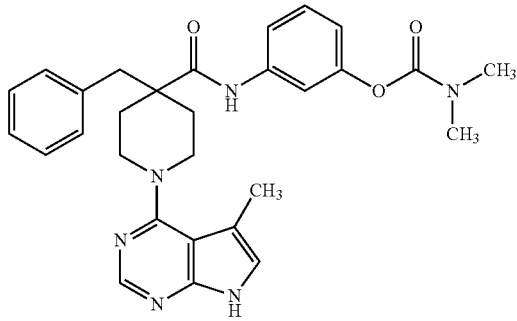 [SMILES: Cc1c[nH]c2ncnc(N3CCC(Cc4ccccc4)(C(=O)Nc4cccc(OC(=O)N(C)C)c4)CC3)c12]

A. Preparation of tert-butyl 4-benzyl-4-(3-(dimethylcarbamoyloxy)phenylcarbamoyl)piperidine-1-carboxylate. Under an atmosphere of N$_2$, 4-benzyl-1-(tert-butoxycarbonyl)piperidine-4-carboxylic acid (0.2 g, 0.626 mmol), pyridine (0.202 mL, 2.5 mmol), and DMF (3 drops) were dissolved in CH$_2$Cl$_2$ (10 mL) and cooled in an ice bath. To the cooled solution, oxalyl chloride (0.06 mL, 0.688 mmol) was added dropwise. The reaction was then removed from the ice bath and stirred at room temperature for 30 min. The reaction was re-cooled in an ice bath, and 3-aminophenyl dimethylcarbamate (0.112 g, 0.626 mmol) was added in one portion. The reaction was stirred overnight, and then washed with 1 N aq. HCl and brine, dried over MgSO$_4$, and concentrated under vacuum. The residue was purified by silica gel chromatography (ethyl acetate:hexanes gradient) to give the title compound in 54% yield. MS (ES+) [M+NH$_4$]$^+$=500.

B. Preparation of 3-(4-benzylpiperidine-4-carboxamido) phenyl dimethylcarbamate. To a solution of tert-butyl 4-benzyl-4-(3-(dimethylcarbamoyloxy)phenylcarbamoyl)piperidine-1-carboxylate from step A (0.162 g, 0.336 mmol) in MeOH (5 mL) was added 4 M HCl in dioxane (0.250 mL, 1.00 mmol). The reaction was heated at 50° C. for 1 hour, and then concentrated under vacuum, re-dissolved in MeOH and re-concentrated twice to give the title compound as the hydrochloride salt. MS (ES+) [M+H]$^+$=382.

C. Preparation of 3-(4-benzyl-1-(5-methyl-7H-pyrrolo[2,3-d]pyrimidin-4-yl)piperidine-4-carboxamido)phenyl dimethylcarbamate. 3-(4-benzylpiperidine-4-carboxamido)phenyl dimethylcarbamate (0.140 g, 0.336 mmol) from step B, 4-chloro-5-methyl-7H-pyrrolo[2,3-d]pyrimidine (0.056 g, 0.336 mmol), N,N-diisopropylethylamine (0.175 mL, 1.00 mmol), and isopropanol (5 mL) were combined and heated at 120° C. overnight in a pressure vessel. The reaction was diluted with CH$_2$Cl$_2$, washed with H$_2$O and brine, dried over MgSO$_4$, and concentrated under vacuum. The residue was taken up in hot ethanol/H$_2$O. Upon cooling, the product precipitated out of solution to give the title compound in 81% yield.

$^1$H NMR (400 MHz, CD$_3$OD) δ ppm 8.18 (s, 1H), 7.15-7.37 (m, 8H), 7.00 (s, 1H), 6.88-6.91 (m, 1H), 3.97 (d, J=13.6 Hz, 2H), 3.25 (t, J=12.24 Hz, 2H), 3.14 (s, 3H), 3.02 (s, 2H), 2.96 (s, 3H), 2.40 (s, 3H), 2.40 (d, J=14.4 Hz, 2H), 1.85-1.92 (m, 2H); MS (ES+) [M+H]$^+$=513.

6.15. Example 15

Synthesis of 3-(4-(benzyloxymethyl)-1-(5-methyl-7H-pyrrolo[2,3-d]pyrimidin-4-yl)piperidine-4-carboxamido)phenyl dimethylcarbamate

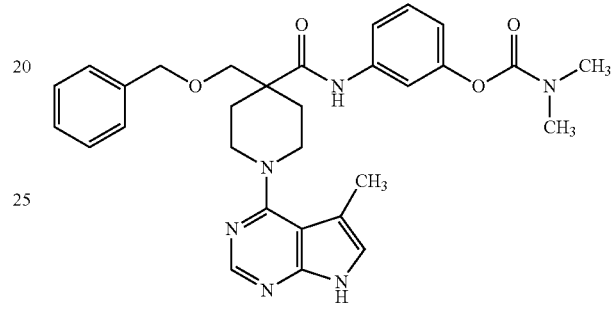

A. Preparation of 1-tert-butyl 4-ethyl 4-(benzyloxymethyl) piperidine-1,4-dicarboxylate. LDA (2.64 mL, 5.82 mmol) was added to a solution of 1-tert-butyl 4-ethyl piperidine-1,4-dicarboxylate (1 g, 3.88 mmol) in THF (35 mL) at −78° C. The reaction was stirred for 30 min, and then BOMCl (0.6 g, 3.88 mmol) was added. The reaction was allowed to warm to room temperature, and then quenched with aq. NH$_4$Cl. The aqueous layer was extracted with EtOAc, and the organic extract was washed with brine, dried over MgSO$_4$, and concentrated under vacuum. The residue was purified by flash chromatography (80 g SiO$_2$, 0-10% ethylacetate:hexanes) to afford the title compound (0.5 g, 34%). MS (ES+) [M+H]$^+$= 378.

B. Preparation of 4-(benzyloxymethyl)-1-(tert-butoxycarbonyl)piperidine-4-carboxylic acid. 1-tert-Butyl 4-ethyl 4-(benzyloxymethyl)piperidine-1,4-dicarboxylate from step A (0.500 g, 1.3 mmol) was dissolved in 1 N aq. LiOH (15 mL) and THF (10 mL) and was heated at 50° C. for 24 hours. The reaction mixture was acidified with 1 N HCl and extracted with Et$_2$O. The organic extract was washed with brine, dried over MgSO$_4$, and concentrated under vacuum to afford the title compound (0.3 g, 65%). MS (ES+) [M+H]$^+$=349.

C. Preparation of tert-butyl 4-(benzyloxymethyl)-4-(3-(dimethylcarbamoyloxy)phenylcarbamoyl)piperidine-1-carboxylate. To a solution of 4-(benzyloxymethyl)-1-(tert-butoxycarbonyl)piperidine-4-carboxylic acid from step B (0.3 g, 0.85 mmol) in isopropyl acetate (10 mL) was added N,N-diisopropylethylamine (0.165 mL, 0.94 mmol) and HATU (0.94 mmol). The reaction was heated at 85° C. for 30 min, and 3-aminophenyl dimethylcarbamate was added to the mixture. The reaction was heated at 85° C. for 2 hours, then worked up by standard procedures. The product was isolated by flash chromatography (40 g SiO$_2$, 0-30% ethylacetate:hexanes) to give the title compound (0.25 g, 57%). MS (ES+) [M+H]$^+$=512.

D. Preparation of 3-(4-(benzyloxymethyl)piperidine-4-carboxamido)phenyl Dimethylcarbamate. tert-Butyl 4-(benzyloxymethyl)-4-(3-(dimethylcarbamoyloxy)phenylcarbamoyl)piperidine-1-carboxylate from step C (0.25 g, 0.49 mmol) was dissolved in isopropanol, treated with 4 N HCl, and stirred for two hours. The reaction mixture was adjusted to pH 7-8 with NaHCO$_3$, and then extracted with Et$_2$O. The organic extracts were concentrated under vacuum to give the title compound (0.2 g, 100%). MS (ES+) [M+H]$^+$=412.

E. Preparation of 3-(4-(benzyloxymethyl)-1-(5-methyl-7H-pyrrolo[2,3-d]pyrimidin-4-yl)piperidine-4-carboxamido)phenyl dimethylcarbamate. To a solution of 3-(4-(benzyloxymethyl)piperidine-4-carboxamido)phenyl dimethylcarbamate from step D (0.2 g, 0.49 mmol) in isopropanol (5 mL) was added N,N-diisopropylethylamine (0.167 mL, 0.98 mmol) and 4-chloro-5-methyl-7H-pyrrolo[2,3-d]pyrimidine (0.08 g, 0.49 mmol). The reaction was heated at 85° C. overnight, diluted with EtOAc, washed with brine, dried over MgSO$_4$, and concentrated under vacuum. The residue was purified by flash chromatography (40 g SiO$_2$, 0-80% ethylacetate:hexanes) to give the title compound (0.1 g, 38%).

$^1$H NMR (400 MHz, CD$_3$OD) δ ppm 10.68 (s, 1H), 8.78 (s, 1H), 8.37 (s, 1H), 7.33-7.44 (m, 6H), 7.25 (t, J=8, 16 Hz, 1H), 7.11 (d, J=8 Hz, 1H), 6.91 (s, 1H), 6.86 (d, J=8 Hz, 1H), 4.62 (s, 2H), 3.65 (s, 2H), 3.62-3.75 (m, 4 H), 3.09 (s, 3H), 3.01 (s, 3H), 2.40 (s, 3H), 2.27-2.33 (m, 2H), 1.75-1.82 (m, 2H); MS (ES+) [M+H]$^+$=543.

6.16. Example 16

Synthesis of 3-(4-(hydroxymethyl)-1-(5-methyl-7H-pyrrolo[2,3-d]pyrimidin-4-yl)piperidine-4-carboxamido)phenyl dimethylcarbamate

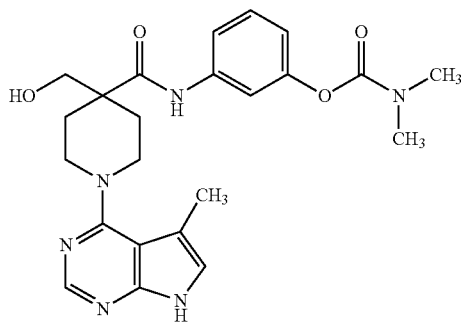 [SMILES: Cc1c[nH]c2ncnc(N3CCC(CO)(C(=O)Nc4cccc(OC(=O)N(C)C)c4)CC3)c12]

To a solution of 3-(4-(benzyloxymethyl)-1-(5-methyl-7H-pyrrolo[2,3-c]pyrimidin-4-yl)piperidine-4-carboxamido) phenyl dimethylcarbamate from example 15, step E, (30 mg, 0.055 mmol) in THF (2 mL) was added Pd/C (10%). The reaction mixture was stirred under H$_2$ at 60 psi overnight. The mixture was filtered and concentrated under vacuum. The residue was purified by prep HPLC (30×250 mm C18 column, 10-100% MeCN:H$_2$O (10 mM NH$_4$OAc), 18 min, 45 mL/min) to give the title compound (1 mg).

$^1$H NMR (400 MHz, CD$_3$OD) δ ppm 8.18 (s, 1H), 7.52 (s, 1H), 7.40-7.42 (m, 1H), 7.33 (t, J=8, 16 Hz, 1H), 7.00 (s, 1H), 6.87 (d, J=8 Hz, 1H), 3.84-3.89 (m, 2H), 3.75 (s, 2H), 3.32-3.44 (m, 2H), 3.14 (s, 3H), 3.00 (s, 3H), 2.45 (s, 3H), 2.38 (d, J=12 Hz, 2H), 1.72-1.81 (m, 2H); MS (ES+) [M+H]$^+$=453.

6.17. Example 17

Synthesis of 3-(4-(methoxymethyl)-1-(5-methyl-7H-pyrrolo[2,3-d]pyrimidin-4-yl)piperidine-4-carboxamido)phenyl dimethylcarbamate

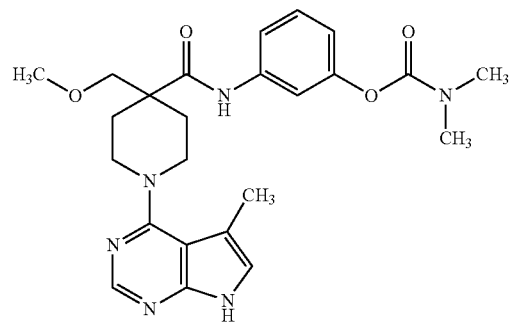

A. Preparation of 1-tert-butyl 4-ethyl 4-(methoxymethyl) piperidine-1,4-dicarboxylate. To a solution of 1-tert-butyl 4-ethyl piperidine-1,4-dicarboxylate (1.0 g, 4.07 mmol) in THF (20 mL) at −78° C. under nitrogen was added dropwise LDA (1.5 M in THF, 4.0 mL, 6.10 mmol). This solution was stirred for 1 hour at −78° C., after which methoxymethyl chloride (0.8 mL, 10.5 mmol) was added. The system was allowed to warm slowly to room temperature over 2 hours. The reaction was quenched with aqueous NH$_4$Cl and extracted with ethyl acetate (3×50 mL). The organic layer was dried over a pad of silica gel, and the solvent removed under vacuum. The title compound was isolated by silica gel chromatography (5-10% ethyl acetate:hexanes) as a clear oil (830 mg, 69% yield). MS (ES+) [M+H]$^+$=302.4.

B. Preparation of 1-(tert-butoxycarbonyl)-4-(methoxymethyl)-piperidine-4-carboxylic acid. To a solution of 1-tert-butyl 4-ethyl 4-(methoxymethyl)piperidine-1,4-dicarboxylate from step A (732 mg, 2.63 mmol) in 1:2 ethanol/water (9 mL) was added lithium hydroxide monohydrate (700 mg). The mixture was heated to 75° C. for 1 hour. The reaction was cooled to room temperature and poured into 50 mL of sat. aq. NaHSO$_4$. The aqueous layer was extracted with ethyl acetate (3×50 mL). The combined organic layers were washed with brine, dried over MgSO$_4$, and concentrated under vacuum to give the title compound as a viscous yellow oil, which was carried on to the next step without further purification. MS (ES+) [M+H]$^+$=274.2.

C. Preparation of tert-butyl 4-(3-(dimethylcarbamoyloxy) phenylcarbamoyl)-4-(methoxymethyl)piperidine-1-carboxylate. To a solution of 1-(tert-butoxycarbonyl)-4-(methoxymethyl)-piperidine-4-carboxylic acid from step B (718 mg, 2.63 mmol), pyridine (0.84 mL, 10.52 mmol), and DMF (catalytic, 3 drops) in CH$_2$Cl$_2$ (13 mL) was added dropwise oxalyl chloride (0.25 mL, 2.89 mmol, caution: exothermic). After gas evolution subsided, the reaction was stirred at ambient temperature for 30 minutes. 3-Aminophenyl dimethylcarbamate (475 mg, 2.63 mmol) was added in one portion to this solution and stirred for another 30 minutes. The reaction was quenched with saturated aqueous NH$_4$Cl, and the aqueous layer was extracted with ethyl acetate (3×50 mL). The combined organic layers were washed with brine, dried over MgSO$_4$, filtered, and concentrated under vacuum. Silica gel chromatography (50% ethyl acetate:hexanes) afforded the title compound (1.03 g, 90% yield for two steps). MS (ES+) [M+NH$_4$]$^+$=453.3

D. Preparation of 3-(4-(methoxymethyl)piperidine-4-carboxamido)phenyl dimethylcarbamate. To a solution of tert-butyl 4-(3-(dimethylcarbamoyloxy)-phenylcarbamoyl)-4-(methoxymethyl)piperidine-1-carboxylate from step C (1.03 g, 2.37 mmol) in methanol (10 mL) was added HCl (4 M solution in dioxane, 2 mL). The reaction was heated at 50° C. for 1 hour, and then concentrated under vacuum to provide the title compound as the hydrochloride salt. MS (ES+) [M+H]$^+$ 336.3.

E. Preparation of 3-(4-(methoxymethyl)-1-(5-methyl-7H-pyrrolo[2,3-d]pyrimidin-4-yl)piperidine-4-carboxamido) phenyl dimethylcarbamate. To a solution of 3-(4-(methoxymethyl)piperidine-4-carboxamido)phenyl dimethylcarbamate, from step D, and N,N-diisopropylethylamine (2 mL, 11.9 mmol) in isopropanol (5 mL) was added 4-chloro-5-methyl-7H-pyrrolo[2,3-d]pyrimidine (397 mg, 2.37 mmol). The reaction mixture was heated to 110° C. in a sealed high-pressure vial for 17 hours, during which time the mixture became homogenous. The reaction was concentrated under vacuum and purified by silica gel chromatography (3-5% methanol:CH$_2$Cl$_2$). The product was washed with cold methanol to provide the title compound as an off-white solid (462 mg, 42% yield).

$^1$H NMR (400 MHz, DMSO-d$_6$) δ ppm 11.50 (br. s., 1H), 9.45 (s, 1H), 8.18 (s, 1H), 7.54-7.57 (m, 1H), 7.47 (d, J=8.84 Hz, 1H), 7.29 (t, J=8.08 Hz, 1H), 7.04 (s, 1H), 6.81 (dd, J=8.08, 2.27 Hz, 1H), 3.68-3.78 (m, 2H), 3.56 (s, 2H), 3.26 (s, 3H), 3.21 (m, 2H), 3.04 (s, 3H), 2.91 (s, 3H), 2.34 (s, 3H), 2.22-2.31 (m, 2H), 1.65-1.78 (m, 2H); MS (ES+) [M+H]$^+$= 467.3.

6.18. Example 18

Synthesis of 3-(4-((2-methoxyethoxy)methyl)-1-(5-methyl-7H-pyrrolo[2,3-d]pyrimidin-4-yl)piperidine-4-carboxamido)phenyl dimethylcarbamate

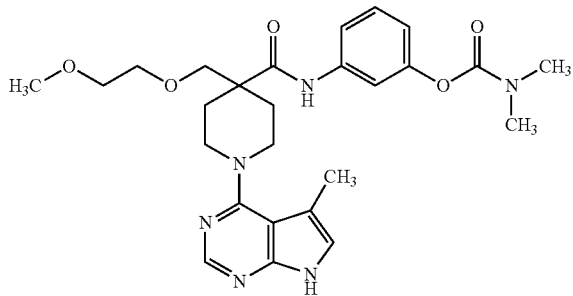

A. Preparation of 1-tert-butyl 4-ethyl 4-((2-methoxyethoxy)methyl)piperidine-1,4-dicarboxylate. To a solution of 1-tert-butyl 4-ethyl piperidine-1,4-dicarboxylate (2.0 g, 7.8 mmol) in THF (70 mL) at −78° C. was added dropwise LDA over 8 minutes, maintaining the temperature below −75° C. The mixture was stirred at −78° C. for 1 hour. 1-Chloromethoxy-2-methoxy-ethane (0.97 g, 7.8 mmol) was added dropwise while maintaining the temperature below −75° C. The mixture was stirred at −78° C. for 3 hours, and then allowed to warm slowly to room temperature overnight. The mixture was quenched with sat. aq. NH$_4$Cl and extracted 3 times with EtOAc. The organics were combined, washed with brine, dried over MgSO$_4$, and concentrated. Silica gel chromatography (10-20% ethyl acetate:hexanes) gave the title compound in 67% yield. MS (ES+) [M+H]$^+$=346.

B. Preparation of 1-(tert-butoxycarbonyl)-4-(2-methoxyethoxy)piperidine-4-carboxylic acid. 1-tert-Butyl 4-ethyl 4-(2-methoxyethoxy)methyl)piperidine-1,4-dicarboxylate from step A (1.78 g, 5.15 mmol) was treated with LiOH (0.62 g. 26 mmol) in ethanol (12 mL) and water (24 mL) at 80° C. for 18 hours. The mixture was cooled, diluted with dichloromethane, and washed with sat. aq. NaHSO$_4$. The aqueous phase was back extracted with dichloromethane (3×), and the organics were combined, washed with brine, dried over MgSO$_4$, and concentrated to give the title compound in quantitative yield. MS (ES+) [M+H]$^+$=318.

C. Preparation of tert-butyl 4-(3-(dimethylcarbamoyloxy) phenylcarbamoyl)-4-(2-methoxyethoxy)piperidine-1-carboxylate. To a solution of 1-(tert-butoxycarbonyl)-4-(2-methoxyethoxy)piperidine-4-carboxylic acid from step B (1.6 g, 5.1 mmol) in dichloroethane was added pyridine (1.6 g, 20 mmol) and DMF (0.05 mL), followed by oxalyl chloride (0.65 g, 5.1 mmol). The mixture was stirred for 30 minutes, and then 3-aminophenyl dimethylcarbamate (0.91 g, 5.04 mmol) was added. The mixture was stirred for 18 hours, then diluted with dichloromethane, washed twice with 1 N aq. HCl and once with brine, dried over MgSO$_4$, and concentrated. Silica gel chromatography (0-5% MeOH:CH$_2$Cl$_2$) gave the title compound in 88% yield. MS (ES+) [M+H]$^+$=480.

D. Preparation of 3-(4-(2-methoxyethoxy)piperidine-4-carboxamido)phenyl dimethylcarbamate. tert-Butyl 4-(3-(dimethylcarbamoyloxy)phenylcarbamoyl)-4-(2-methoxyethoxy)piperidine-1-carboxylate from step C (2.1 g, 4.4 mmol) was treated with HCl (4.0 N in dioxane, 5.5 mL, 22 mmol) in methanol (20 mL) at 50° C. for 30 minutes. The mixture was concentrated to give the title compound as the hydrochloride salt in quantitative yield. MS (ES+) [M+H]$^+$= 380.

E. Preparation of 3-(4-((2-methoxyethoxy)methyl)-1-(5-methyl-7H-pyrrolo[2,3-d]pyrimidin-4-yl)piperidine-4-carboxamido)phenyl dimethylcarbamate. 3-(4-(2-Methoxyethoxy)piperidine-4-carboxamido)phenyl dimethylcarbamate from step D (1.82 g, 4.38 mmol), 4-chloro-5-methyl-7H-pyrrolo[2,3-c]pyrimidine (0.73 g, 4.4 mmol), N,N-diisopropylethylamine (2.8 g. 22 mmol), and isopropanol (50 mL) were combined in a pressure rated sealed tube and heated at 115° C. for 18 hours. The mixture was concentrated and chromatographed (SiO$_2$, 0-5% MeOH: CH$_2$Cl$_2$) to give the title compound in 61% yield.

$^1$H NMR (400 MHz, DMSO-d$_6$) δ ppm 11.48 (s, 1H), 9.43 (s, 1H), 8.18 (s, 1H), 7.52 (s, 1H), 7.44 (d, J=8 Hz, 1H), 7.30 (t, J=8 and 16 Hz, 1H), 7.05 (s, 1H), 6.81 (d, J=8 Hz, 1H), 3.68-3.76 (m, 2H), 3.67 (s, 2H), 3.55-3.58 (m, 2H), 3.44-3.47 (m, 2H), 3.24-3.30 (m, 2H), 3.23 (s, 3H), 3.04 (s, 3H), 2.91 (s, 3H), 2.35 (s, 3H), 2.26 (d, J=16 Hz, 2H), 1.69-1.76 (m, 2H); MS (ES+) [M+H]$^+$=511.

6.19. Example 19

Synthesis of 3-(4-((benzyloxycarbonylamino)methyl)-1-(5-methyl-7H-pyrrolo[2,3-d]pyrimidin-4-yl)piperidine-4-carboxamido)phenyl dimethylcarbamate

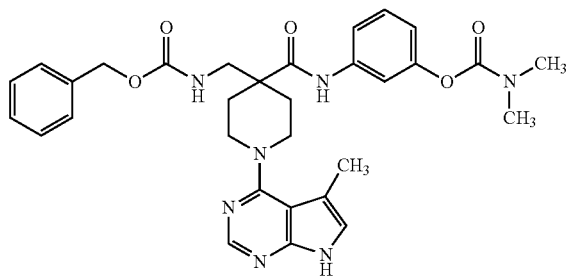 [SMILES: Cc1c[nH]c2ncnc(N3CCC(CNC(=O)OCc4ccccc4)(C(=O)Nc4cccc(OC(=O)N(C)C)c4)CC3)c12]

A. Preparation of 1-tert-butyl 4-methyl 4-((benzyloxycarbonylamino)methyl)piperidine-1,4-dicarboxylate. To a solution of 1-tert-butyl 4-methyl 4-(aminomethyl)piperidine-1,4-dicarboxylate (0.300 g, 1.1 mmol) and N,N-diisopropylethylamine (0.229 mL, 1.32 mmol) in $CH_2Cl_2$ (5 mL) at 0° C. was added benzyl chloroformate. The reaction was stirred overnight, and then diluted with $CH_2Cl_2$ and washed with $H_2O$ and brine, dried over $MgSO_4$, and concentrated under vacuum. The residue was purified by silica gel chromatography (EtOAc:hexanes gradient) to give the title compound in 82% yield. MS (ES+) $[M+H]^+$=407.

B. Preparation of 4-((benzyloxycarbonylamino)methyl)-1-(tert-butoxycarbonyl)piperidine-4-carboxylic acid. To a solution of 1-tert-butyl 4-methyl 4-((benzyloxycarbonylamino)methyl)piperidine-1,4-dicarboxylate from step A in methanol (5 mL) was added 1 N aq. NaOH (0.615 mL, 0.615 mmol). The reaction was heated at 50° C. overnight, acidified to pH 5 with 1 N aq. HCl, and extracted 3× with $CH_2Cl_2$. The combined organic extracts were washed with brine, dried over $Na_2SO_4$, and concentrated under vacuum to give the title compound, which was carried on crude. MS (ES+) $[M+H]^+$ 393.

C. Preparation of tert-butyl 4-((benzyloxycarbonylamino)methyl)-4-(3-(dimethylcarbamoyloxy)phenylcarbamoyl)piperidine-1-carboxylate. Under an atmosphere of $N_2$, 4-((benzyloxycarbonylamino)methyl)-1-(tert-butoxycarbonyl)piperidine-4-carboxylic acid (0.240 g, 0.611 mmol) from step B, pyridine (0.197 mL, 2.44 mmol) and DMF (3 drops) were dissolved in $CH_2Cl_2$ (10 mL) and cooled in an ice bath. Oxalyl chloride (0.064 mL, 0.733 mmol) was added dropwise to the solution. The reaction was then removed from the ice bath and stirred at room temperature for 30 minutes. The reaction was re-cooled in an ice bath, and 3-aminophenyl dimethylcarbamate (0.110 g, 0.611 mmol) was added in one portion. The reaction was stirred overnight, and then washed 1 N aq. HCl and brine, dried over $MgSO_4$, and concentrated under vacuum. The residue was purified by silica gel chromatography (ethyl acetate:hexanes gradient) to give the title compound in 72% yield. MS (ES+) $[M+NH_4]^+$=573.

D. Preparation of 3-(4-((benzyloxycarbonylamino)methyl)piperidine-4-carboxamido)phenyl dimethylcarbamate. To a solution of tert-butyl 4-((benzyloxycarbonylamino)methyl)-4-(3-(dimethylcarbamoyloxy)phenylcarbamoyl)piperidine-1-carboxylate from step C (0.245 g, 0.441 mmol) in MeOH (2 mL) was added 4 M HCl in dioxane (0.331 mL, 1.32 mmol). The reaction was heated at 50° C. for 1 hour, and then concentrated under vacuum, re-dissolved in MeOH and re-concentrated twice to give the title compound as the hydrochloride salt. MS (ES+) $[M+H]^+$=455.

E. Preparation of 3-(4-((benzyloxycarbonylamino)methyl)-1-(5-methyl-7H-pyrrolo[2,3-d]pyrimidin-4-yl)piperidine-4-carboxamido)phenyl dimethylcarbamate. 3-(4-((Benzyloxycarbonylamino)methyl)piperidine-4-carboxamido)phenyl dimethylcarbamate (0.216 g, 0.441 mmol) from step D, 4-chloro-5-methyl-7H-pyrrolo[2,3-d]pyrimidine (0.073 g, 0.441 mmol), N,N-diisopropylethylamine (0.230 mL, 1.32 mmol), and isopropanol (5 mL) were combined and heated at 120° C. overnight in a pressure vessel. The crude reaction was diluted with $CH_2Cl_2$ and washed with $H_2O$ and brine, dried over $MgSO_4$, and concentrated under vacuum. The residue was purified by silica gel chromatography (MeOH:$CH_2Cl_2$ gradient) to give the title compound in 54% yield.

$^1$H NMR (400 MHz, $CD_3OD$) δ ppm 8.18 (s, 1H), 7.49 (s, 1H), 7.40 (d, J=8 Hz, 1H), 7.26-7.34 (m, 6H), 7.00 (s, 1H), 6.89 (d, J=8 Hz, 1H), 5.06 (s, 2H), 3.92 (d, J=13.2 Hz, 2H), 3.50 (s, 2H), 3.28-3.37 (m, 2H), 3.1 (s, 3H), 2.99 (s, 3H), 2.43 (s, 3H), 2.40 (d, J=12 Hz, 2H), 1.79 (t, J=10.6, 21.2 Hz, 2H); MS (ES+) $[M+H]^+$=586.

6.20. Example 20

Synthesis of 3-(4-(aminomethyl)-1-(5-methyl-7H-pyrrolo[2,3-d]pyrimidin-4-yl)piperidine-4-carboxamido)phenyl dimethylcarbamate

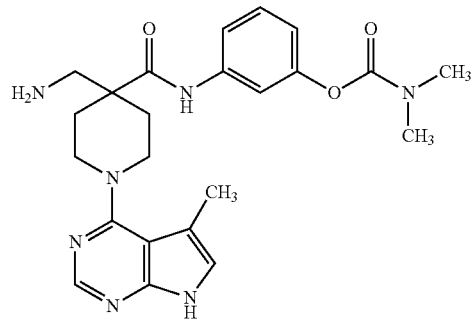 [SMILES: Cc1c[nH]c2ncnc(N3CCC(CN)(C(=O)Nc4cccc(OC(=O)N(C)C)c4)CC3)c12]

3-(4-((Benzyloxycarbonylamino)methyl)-1-(5-methyl-7H-pyrrolo[2,3-d]pyrimidin-4-yl)piperidine-4-carboxamido)phenyl dimethylcarbamate (0.140 g, 0.239 mmol) from example 19, step E, Pd/C (10% Pd/C, Pearlman), and methanol (5 mL) were combined and hydrogenated overnight at 1 atmosphere. The reaction was filtered through celite, concentrated under vacuum, and purified by neutral phase prep-HPLC to give the title compound as the acetate salt in 52% yield.

$^1$H NMR (400 MHz, $D_2O$) δ ppm 7.90 (s, 1H), 7.30 (t, J=8, 6 Hz, 1H), 7.18-7.19 (m, 2H), 6.84-6.88 (m, 1H), 3.48 (d, J=13.6 Hz, 2H), 3.20 (s, 2H), 3.08 (t, J=10.8, 21.6 Hz, 2H), 2.96 (s, 3H), 2.83 (s, 3H), 2.27 (d, J=14.4 Hz, 2H), 2.11 (s, 3H), 1.72 (t, J=10, 20 Hz, 2H); MS (ES+) $[M+H]^+$=452.

6.21. Example 21

Synthesis of 3-(4-((dimethylamino)methyl)-1-(5-methyl-7H-pyrrolo[2,3-d]pyrimidin-4-yl)piperidine-4-carboxamido)phenyl dimethylcarbamate

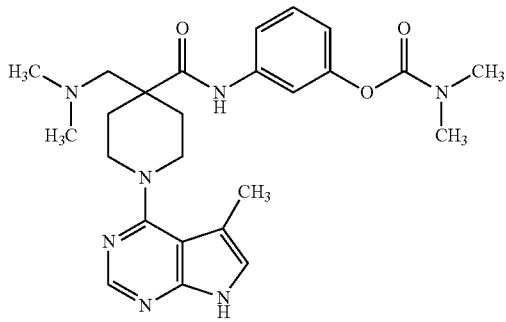

To a solution of the acetate salt of 3-(4-(aminomethyl)-1-(5-methyl-7H-pyrrolo[2,3-d]pyrimidin-4-yl)piperidine-4-carboxamido)phenyl dimethylcarbamate from example 20 (14 mg, 0.027 mmol), acetic acid (6.2 µl, 0.11 mmol), and NaBH$_3$CN (2.1 mg, 0.034 mmol) was added formaldehyde (37% in H$_2$O, 48 µl, 0.064 mmol). The reaction was stirred overnight, then concentrated, and the residue was purified by prep HPLC (30×100 mm C18 column, 5-70% MeCN:H$_2$O (10 mM NH$_4$OAc), 12 min, 45 mL/min.) and lyophilized to give the title compound (8 mg, 0.014 mmol, 57%) as the acetate salt.

$^1$H NMR (400 MHz, CD$_3$OD) δ ppm 8.18 (s, 1 H), 7.51 (t, J=2.02 Hz, 1 H), 7.37-7.42 (m, 1 H), 7.34 (t, J=8.08 Hz, 1 H), 7.00 (s, 1 H), 6.85-6.91 (m, 1 H), 3.89 (d, J=13.64 Hz, 2 H), 3.38-3.48 (m, 2 H), 3.14 (s, 3 H), 3.01 (s, 3 H), 2.72 (s, 2 H), 2.36-2.45 (m, 11 H), 1.79 (ddd, J=13.71, 10.42, 3.41 Hz, 2 H); MS (ES+) [M+H]$^+$=480.

6.22. Example 22

Synthesis of 3-(4-(2-(dimethylamino)ethyl)-1-(5-methyl-7H-pyrrolo[2,3-d]pyrimidin-4-yl)piperidine-4-carboxamido)phenyl dimethylcarbamate

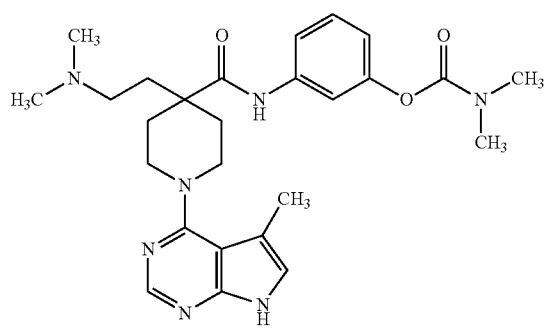

A. Preparation of 1-tert-butyl 4-ethyl 4-(2-(dimethylamino)ethyl)piperidine-1,4-dicarboxylate. To a solution of 1-tert-butyl 4-ethyl piperidine-1,4-dicarboxylate (514 mg, 2 mmol) in THF (10 mL) at −78° C. was added dropwise LDA (1.5 M in cyclohexane, 2 mL, 3 mmol). After stirring for 30 minutes, 2-bromo-N,N-dimethylethanamine (370 mg, 2.4 mmol) in THF (3 mL) was added. The reaction was stirred for 30 min at −78° C., then allowed to warm to room temperature, stirred for 2 hours, then quenched with sat. aq. NaHCO$_3$, diluted with EtOAc, washed with sat. aq. NaHCO$_3$ and brine (with back extraction), dried over MgSO$_4$, and concentrated under vacuum. The residue was purified by flash chromatography (40 g SiO$_2$, 0-15% MeOH:CH$_2$Cl$_2$) to give the title compound (328 mg, 1.0 mmol, 50%) as a yellow oil. MS (ES+) [M+H]$^+$=329.

B. Preparation of 1-(tert-butoxycarbonyl)-4-(2-(dimethylamino)ethyl)piperidine-4-carboxylic acid. 1-tert-Butyl 4-ethyl 4-(2-(dimethylamino)ethyl)piperidine-1,4-dicarboxylate from step A (328 mg, 1.0 mmol) was treated overnight with lithium hydroxide monohydrate (210 mg, 5 mmol) in 1:1 EtOH:H$_2$O (5 mL) at 60° C. The reaction was cooled to room temperature, neutralized to pH 6 with 1 N aq. HCl, and concentrated under vacuum. The residue was purified by prep HPLC and lyophilized twice to give the title compound (191 mg, 64%) as a white solid. MS (ES+) [M+H]$^+$=301.

C. Preparation of tert-butyl 4-(2-(dimethylamino)ethyl)-4-(3-(dimethylcarbamoyloxy)phenylcarbamoyl)piperidine-1-carboxylate. 1-(tert-Butoxycarbonyl)-4-(2-(dimethylamino)ethyl)piperidine-4-carboxylic acid from step B (100 mg, 0.33 mmol), HATU (175 mg, 0.46 mmol), and N,N-diisopropylethylamine (0.116 mL, 0.67 mmol) were stirred in isopropyl acetate for 10 minutes. 3-aminophenyl dimethylcarbamate (90 mg, 0.5 mmol) was added, and the reaction was stirred at 85° C. for 2 hours, cooled to room temperature, stirred overnight, and then diluted with EtOAc, washed with sat. aq. Na$_2$CO$_3$ and brine (with back extraction), dried over MgSO$_4$, filtered, and concentrated under vacuum, to give the title compound as a viscous oil. MS (ES+) [M+H]$^+$=463.

D. Preparation of 3-(4-(2-(dimethylamino)ethyl)piperidine-4-carboxamido)phenyl dimethylcarbamate. Crude tert-butyl 4-(2-(dimethylamino)ethyl)-4-(3-(dimethylcarbamoyloxy)phenylcarbamoyl)piperidine-1-carboxylate from step C was treated with 1:1 TFA:CH$_2$Cl$_2$ (1.5 mL) for 45 min. The reaction was concentrated under vacuum, and the residue was purified by prep HPLC (30×100 mm C18 column, 0-50% MeOH:H$_2$O (0.1% TFA), 12 min., 45 mL/min.) and lyophilized to give impure title compound (173 mg) as the TFA salt. MS (ES+) [M+H]$^+$363.

E. Preparation of 3-(4-(2-(dimethylamino)ethyl)-1-(5-methyl-7H-pyrrolo[2,3-d]pyrimidin-4-yl)piperidine-4-carboxamido)phenyl dimethylcarbamate. Impure 3-(4-(2-(dimethylamino)ethyl)piperidine-4-carboxamido)phenyl dimethylcarbamate from step D (173 mg) was combined with 4-chloro-5-methyl-7H-pyrrolo[2,3-d]pyrimidine (50 mg, 0.30 mmol) and N,N-diisopropylethylamine (0.174 mL, 5 mmol) in isobutanol (0.4 mL) and heated at 110° C. for 7 hours. The reaction was cooled to room temperature and concentrated under vacuum. The residue was purified by prep HPLC (30×100 mm C18 column, 10-70% MeCN:H$_2$O (10 mM NH$_4$OAc), 12 min, 45 mL/min) and lyophilized to give the title compound (60 mg) as the di-acetate salt.

$^1$H NMR (400 MHz, CD$_3$OD) δ ppm 8.19 (s, 1 H), 7.52 (t, J=2.15 Hz, 1 H), 7.44 (d, J=8.08 Hz, 1 H), 7.35 (t, J=8.08 Hz, 1 H), 7.01 (s, 1 H), 6.91 (dd, J=7.58, 1.77 Hz, 1 H), 3.91 (d, J=13.64 Hz, 2 H), 3.37-3.30 (m, 2 H), 3.14 (s, 3 H), 3.01 (s, 3 H), 2.75-2.82 (m, 2 H), 2.58 (s, 6 H), 2.43-2.47 (m, 5 H), 2.00-2.08 (m, 2 H), 1.79-1.89 (m, 2 H); MS (ES+) [M+H]$^+$=494.

6.23. Example 23

Synthesis of 3-(4-((1H-imidazol-4-yl)methyl)-1-(5-methyl-7H-pyrrolo[2,3-d]pyrimidin-4-yl)piperidine-4-carboxamido)phenyl dimethylcarbamate

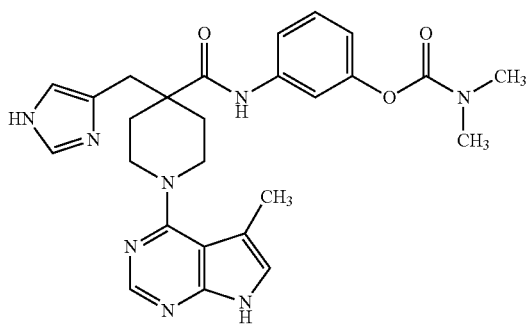 [SMILES: Cc1c[nH]c2ncnc(N3CCC(Cc4c[nH]cn4)(C(=O)Nc4cccc(OC(=O)N(C)C)c4)CC3)c12]

A. Preparation of 1-tert-butyl 4-ethyl 4-((1-trityl-1H-imidazol-4-yl)methyl) piperidine-1,4-dicarboxylate. To a solution of 1-tert-butyl 4-ethyl piperidine-1,4-dicarboxylate (360 mg, 1.39 mmol) in anhydrous THF (10 mL) at −78° C. was added LDA (1.7 M in THF, 1.07 mL, 1.8 mmol) dropwise over 10 min. The reaction mixture was stirred at −78° C. for 1 hour, and 4-(chloromethyl)-1-trityl-1H-imidazole (500 mg, 13.9 mmol) in THF (5 mL) was added slowly. The reaction mixture was allowed to warm to room temperature over 1 hour, quenched with sat. aq. NH$_4$Cl (10 mL), and extracted with EtOAc (3×20 mL). The combined organic extracts were washed with brine, dried over Na$_2$SO$_4$, filtered, and concentrated under vacuum. Purification by silica gel chromatography (10-50% EtOAc:Hexanes) afforded the title compound (403 mg, 51%). MS (ES+) [M+H]$^+$580.3.

B. Preparation of 1-(test-butoxycarbonyl)-4-((1-trityl-1H-imidazol-4-yl)methyl)piperidine-4-carboxylic acid. To a solution of 1-tert-butyl 4-ethyl 4-((1-trityl-1H-imidazol-4-yl)methyl)piperidine-1,4-dicarboxylate from step A (330 mg, 0.57 mmol) in 1:1:2 THF:MeOH:H$_2$O (10 mL) was added LiOH (136 mg, 5.7 mmol). The mixture was refluxed until LCMS showed complete conversion to product, then concentrated under vacuum, dissolved in water (3 mL), neutralized to pH 5-6 with aq. NaHSO$_4$, and extracted with ethyl acetate (3×10 mL). The combined organic phases were washed with brine, dried over Na$_2$SO$_4$, and concentrated under vacuum to give the title compound (273 mg, 86%). MS (ES+) [M+H]$^+$ 552.2.

C. Preparation of tert-butyl 4-(3-(dimethylcarbamoyloxy)phenylcarbamoyl)-4-((1-trityl-1H-imidazol-4-yl)methyl)piperidine-1-carboxylate. To a solution of 1-(tert-butoxycarbonyl)-4-((1-trityl-1H-imidazol-4-yl)methyl)piperidine-4-carboxylic acid from step B (270 mg, 0.6 mmol) in isopropyl acetate (5 mL) were added HATU (273 mg, 0.73 mmol) and N,N-diisopropylethylamine (205 μL, 1.2 mmol). The mixture was stirred for 5 min, and 3-aminophenyl dimethylcarbamate (108 mg, 0.6 mmol) was added. The resulting mixture was heated at 90° C. for 2 hours. The reaction mixture was diluted with EtOAc (10 mL), washed with aqueous NaHCO$_3$ and brine, dried over Na$_2$SO$_4$, filtered, and concentrated under vacuum. The residue was purified by silica gel chromatography (10-70% EtOAc:Hexanes) to afford the title compound (185 mg, 43%). MS (ES+) [M+H]$^+$=714.2.

D. Preparation of 3-(4-((1H-imidazol-4-yl)methyl)piperidine-4-carboxamido) phenyl dimethylcarbamate. To a solution of tert-butyl 4-(3-(dimethylcarbamoyloxy)phenylcarbamoyl)-4-((1-trityl-1H-imidazol-4-yl)methyl)piperidine-1-carboxylate from step C (180 mg) in MeOH (5 mL) was added HCl (1 N in dioxane, 1 mL). The reaction was heated at 60° C. for 1 hour, and then concentrated under vacuum. The residue was dissolved in EtOAc (5 mL), washed with aq. NaHCO$_3$ and brine, dried over Na$_2$SO$_4$, filtered, and concentrated under vacuum to produce the title compound (84 mg, 93%). MS (ES+) [M+H]$^+$=372.2.

E. Preparation of 3-(4-((1H-imidazol-4-yl)methyl)-1-(5-methyl-7H-pyrrolo[2,3-d]pyrimidin-4-yl)piperidine-4-carboxamido)phenyl dimethylcarbamate. 3-(4-((1H-imidazol-4-yl)methyl)piperidine-4-carboxamido) phenyl dimethylcarbamate from step D (10 mg, 0.027 mmol), 4-chloro-5-methyl-7H-pyrrolo[2,3-d]pyrimidine (5 mg, 0.03 mmol), and N,N-diisopropylethylamine (23 μL, 0.135 mmol) were combined in isopropanol (0.5 mL). The resulting mixture was heated at 100° C. in a sealed pressure tube for 24 hours. The reaction mixture was cooled and concentrated under vacuum. The residue was purified by prep HPLC (10-95% MeOH:H$_2$O with 0.1% HCOOH), then treated with AcOH in H$_2$O and lyophilized to give the title compound (5.7 mg, 42%) as the acetate salt.

$^1$H NMR (400 MHz, CD$_3$OD) δ ppm 8.17 (s, 1 H), 7.61 (s, 1 H), 7.42-7.45 (m, 1 H), 7.31-7.39 (m, 2 H), 6.99-7.01 (m, 1 H), 6.87-6.91 (m, 1 H), 6.79 (s, 1 H), 3.90-3.98 (m, 2 H, 3.14 (s, 3 H, 3.02 (br. s., 2 H), 3.01 (s, 3 H, 2.44 (d, J=1.01 Hz, 3 H, 2.36-2.43 (m, 2 H), 1.94 (s, 3 H, 1.83-1.93 (m, 4 H; MS (ES+) [M+H]$^+$=503.3.

6.24. Example 24

Synthesis of 3-(4-(benzyloxy)-1-(5-methyl-7H-pyrrolo[2,3-d]pyrimidin-4-yl)piperidine-4-carboxamido)phenyl dimethylcarbamate

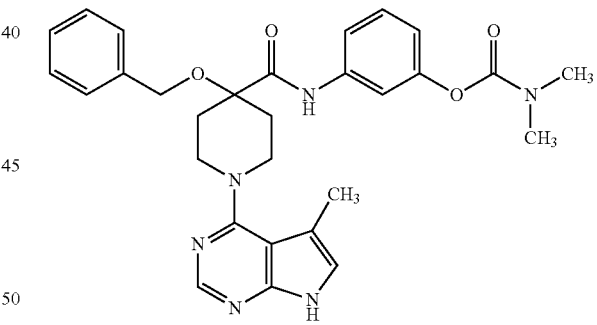

A. Preparation of 1-tert-butyl 4-methyl 4-hydroxypiperidine-1,4-dicarboxylate. To a solution of methyl 4-hydroxypiperidine-4-carboxylate (prepared as described in U.S. patent application no. 2005/0080095 to Zheng et al., filed on Apr. 14, 2005) (792 mg, 4.98 mmol) and triethylamine (1.04 mL, 7.47 mmol) in dichloromethane (25 mL) was added di-tert-butyl dicarbonate (1.26 mL, 5.48 mmol). Reaction progress was monitored by TLC analysis/ELSD. Upon completion, volatiles were removed under vacuum. Silica gel chromatography (0-10% MeOH:CH$_2$Cl$_2$) provided the title compound as a clear oil (1.25 g, 99% yield). MS (ES+) [M+H]$^+$=250.2.

B. Preparation of 1-tert-butyl 4-methyl 4-(benzyloxy)piperidine-1,4-dicarboxylate. To a solution of 1-tert-butyl 4-methyl 4-hydroxypiperidine-1,4-dicarboxylate from step A (535 mg, 2.06 mmol) in DMF (8.2 mL) was carefully added sodium hydride (60% dispersion in mineral oil, 124 mg, 3.09 mmol). The mixture was stirred for 30 minutes at room temperature. Benzyl bromide (0.29 mL, 2.47 mmol) was added, and the reaction was stirred for another 30 minutes. Upon completion as monitored by TLC analysis, the reaction was quenched with 50 mL of 1:1 saturated aq. NH$_4$Cl:water. The aqueous layer was extracted with ethyl acetate (3×50 mL). The combined organic layers were washed with brine, dried with MgSO$_4$, and concentrated under vacuum. Silica gel chromatography (5-10% ethyl acetate:hexanes) provided the title compound as a clear oil (359 mg, 54% yield). MS (ES+) [M+H]$^+$=340.3.

C. Preparation of 1-(tert-butoxycarbonyl)-4-(benzyloxy)-piperidine-4-carboxylic acid. To a solution of 1-tert-butyl 4-methyl 4-(benzyloxy)piperidine-1,4-dicarboxylate from step B (350 mg, 1.00 mmol) in 1:2 methanol/water (6 mL) was added lithium hydroxide monohydrate (200 mg). The mixture was heated to 60° C. for 30 min, and then cooled to room temperature and poured onto saturated aqueous NaHSO$_4$ (25 mL). The aqueous layer was extracted with ethyl acetate (3×25 mL). The combined organic layers were washed with brine, dried with MgSO$_4$, and concentrated under vacuum to give the title compound as a viscous oil, which was carried on to the next step without further purification.

D. Preparation of tert-butyl 4-(benzyloxy)-4-(3-(dimethyl-carbamoyloxy)phenyl-carbamoyl)piperidine-1-carboxylate. To a solution of 1-(tert-butoxycarbonyl)-4-(benzyloxy)-piperidine-4-carboxylic acid from step C (335 mg, 1.00 mmol), pyridine (0.43 mL, 5.40 mmol), and DMF (catalytic, 3 drops) in CH$_2$Cl$_2$ (6.8 mL) was added dropwise oxalyl chloride (0.13 mL, 1.49 mmol, caution: exothermic). After gas evolution subsided, the reaction was stirred at ambient temperature for 30 minutes. 3-Aminophenyl dimethylcarbamate (244 mg, 1.35 mmol) was added in one portion to this solution, which was stirred for another 30 minutes. The reaction was quenched with saturated aqueous NH$_4$Cl, and the aqueous layer was extracted with ethyl acetate (3×50 mL). The combined organic layers were washed with brine, dried with MgSO$_4$, filtered, and concentrated under vacuum. Silica gel chromatography (40% ethyl acetate:hexanes) afforded the title compound as a white solid (406 mg, 82% yield. MS (ES+) [M+NH$_4$]$^+$=515.4.

E. Preparation of 3-(4-(benzyloxy)piperidine-4-carboxamido)phenyl dimethyl-carbamate. To a solution of tert-butyl 4-(benzyloxy)-4-(3-(dimethylcarbamoyloxy)-phenylcarbamoyl)piperidine-1-carboxylate from step D (400 mg, 0.804 mmol) in methanol (4 mL) was added HCl (4 M solution in dioxane, 0.8 mL). The reaction was heated at 50° C. for 1 hour, and then concentrated under vacuum to provide the title compound as the hydrochloride salt. MS (ES+) [M+H]$^+$=398.4.

F. Preparation of 3-(4-(benzyloxy)-1-(5-methyl-7H-pyrrolo[2,3-d]pyrimidin-4-yl)piperidine-4-carboxamido)phenyl dimethylcarbamate. To a solution of 3-(4-(benzyloxy)piperidine-4-carboxamido)phenyl dimethylcarbamate, from step E, and N,N-diisopropylethylamine (0.7 mL, 4.02 mmol) in isopropanol (1.6 mL) was added 4-chloro-5-methyl-7H-pyrrolo[2,3-d]pyrimidine (135 mg, 0.804 mmol). The reaction mixture was heated to 110° C. in a sealed high-pressure vial for 17 hours, during which time the mixture became homogenous. The reaction was concentrated under vacuum, and half of the material was purified by prep HPLC (30×100 mm C18 column, 20-100% acetonitrile:water (10 mM ammonium acetate), 15 min, 45 mL/min) to afford the title compound (33.4 mg) as a white solid.

$^1$H NMR (400 MHz, CD$_3$OD) δ ppm 9.71-9.74 (br. s., 1H), 8.22 (s, 1H), 7.51 (app q, J=1.85 Hz, 1H), 7.44-7.49 (m, 2H), 7.29-7.42 (m, 5H), 7.03 (d, J=1.01 Hz, 1H), 6.89 (ddd, J=7.83, 2.27, 1.26 Hz, 1H), 4.54 (s, 2H), 3.91-3.99 (m, 2H), 3.45-3.54 (m, 2H), 3.14 (s, 3H), 3.01 (s, 3H), 2.46 (d, J=1.01 Hz, 3H), 2.22-2.36 (m, 4H); MS (ES+) [M+H]$^+$=529.3.

6.25. Example 25

Synthesis of 3-(4-hydroxy-1-(5-methyl-7H-pyrrolo[2,3-d]pyrimidin-4-yl)piperidine-4-carboxamido) phenyl dimethylcarbamate

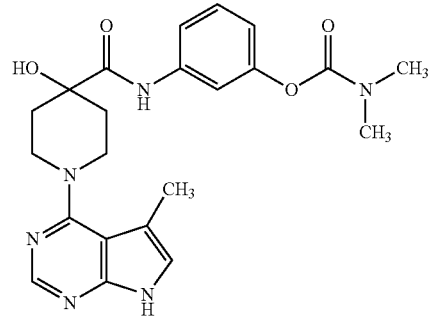 [SMILES: Cc1c[nH]c2ncnc(N3CCC(O)(C(=O)Nc4cccc(OC(=O)N(C)C)c4)CC3)c12]

Crude 3-(4-(benzyloxy)-1-(5-methyl-7H-pyrrolo[2,3-d]pyrimidin-4-yl)piperidine-4-carboxamido)phenyl dimethylcarbamate from example 24, step F (85% pure, approximately 80 mg) was taken up in methanol (2 mL), and a catalytic amount of Pearlman's catalyst was added. The system was hydrogenated at 60 psi for 24 hours, after which a small amount of product was observed. Trifluoroacetic acid (0.1 mL) was added, and the hydrogenation was continued at 60 psi H$_2$ for 3 days, after which the reaction was approximately one third of the way completed. The reaction was filtered, and the product was isolated by prep HPLC (30×100 mm C18 column, 10-100% acetonitrile:water (10 mM ammonium acetate), 15 min, 45 mL/min) to afford the title compound (9.6 mg) as a white solid.

$^1$H NMR (400 MHz, CD$_3$OD) δ ppm 8.20 (s, 1H), 7.55 (t, J=2.02 Hz, 1H), 7.44 (ddd, J=8.08, 2.02, 1.01 Hz, 1H), 7.33 (t, J=8.08 Hz, 1H), 6.99 (app. d., J=1.01 Hz, 1H), 6.87 (ddd, J=8.08, 2.27, 0.76 Hz, 1H), 3.95-4.03 (m, 2H), 3.73 (s, 3H), 3.41 (dt, J=12.63, 2.27 Hz, 2H), 3.13-3.26 (m, 2H), 3.12 (s, 3H), 2.99 (s, 3H), 2.44 (d, J=0.76 Hz, 3H), 2.36 (dt, J=13.39, 4.29 Hz, 2H), 1.75-1.83 (m, 2H). MS (ES+) [M+H]$^+$=439.3.

6.26. Example 26

Synthesis of 3-(4-(2-methoxyethoxy)-1-(5-methyl-7H-pyrrolo[2,3-d]pyrimidin-4-yl)piperidine-4-carboxamido)phenyl dimethylcarbamate

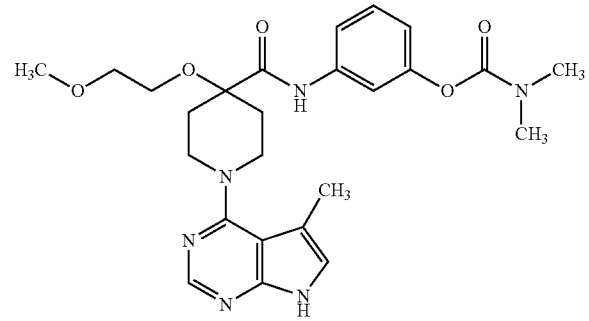

A. Preparation of 1-tert-butyl 4-methyl 4-(2-methoxyethoxy)piperidine-1,4-dicarboxylate. To a solution of 1-tert-butyl 4-methyl 4-hydroxypiperidine-1,4-dicarboxylate (360 mg, 1.39 mmol) in DMF (5.6 mL) was carefully added sodium hydride (60% dispersion in mineral oil, 84 mg, 2.08 mmol). The mixture was stirred for 30 minutes at room temperature. 1-Chloro-2-methoxyethane (0.38 mL, 4.17 mmol) was added, and the reaction was stirred at 60° C. for 72 hours. The reaction was quenched with 25 mL of water. The aqueous layer was extracted with ethyl acetate (3×25 mL). The combined organic layers were washed with brine, dried with MgSO$_4$, and concentrated under vacuum. Silica gel chromatography (20-35% ethyl acetate:hexanes) provided the title compound and starting material as a mixture that was carried forward (150 mg, 1:2 product:starting material).

B. Preparation of 1-(tert-butoxycarbonyl)-4-(2-methoxyethoxy)piperidine-4-carboxylic acid. The product mixture from step A (150 mg) was taken up in 1:2 methanol:water (3 mL). Lithium hydroxide monohydrate (150 mg) was added, and the mixture was heated to 60° C. for 2 hours. The reaction was cooled to room temperature and poured onto saturated aqueous NaHSO$_4$ (25 mL). The aqueous layer was extracted with ethyl acetate (3×25 mL). The combined organic layers were washed with brine, dried with MgSO$_4$, and concentrated under vacuum to give a 2:1 mixture of 1-(tert-butoxycarbonyl)-4-hydroxypiperidine-4-carboxylic acid and 1-(tert-butoxycarbonyl)-4-(2-methoxyethoxy)piperidine-4-carboxylic acid, respectively, as a viscous oil, which was carried on to the next step without further purification. MS (ES+) [M+H]$^+$=304.2.

C. Preparation of tert-butyl 4-(3-(dimethylcarbamoyloxy)phenylcarbamoyl)-4-(2-methoxyethoxy)piperidine-1-carboxylate. To a solution of carboxylic acids from step B, pyridine (0.2 mL, 2.48 mmol), and DMF (catalytic, 2 drops) in CH$_2$Cl$_2$ (3.1 mL) was added dropwise oxalyl chloride (60 µL, 0.68 mmol, caution: exothermic). After gas evolution subsided, the reaction was stirred at ambient temperature for 30 minutes. 3-Aminophenyl dimethylcarbamate (112 mg, 0.62 mmol) was added in one portion to this solution, which was stirred for another 30 minutes. The reaction was quenched with saturated aq. NH$_4$Cl, and the aqueous layer was extracted with ethyl acetate (3×50 mL). The combined organic layers were washed with brine, dried with MgSO$_4$, filtered, and concentrated under vacuum. Silica gel chromatography (80% ethyl acetate:hexanes) afforded the title compound as an off-white solid (150 mg). MS (ES+) [M+CH$_3$CN]$^+$=529.3.

D. Preparation of 3-(4-(2-methoxyethoxy)piperidine-4-carboxamido)phenyl dimethylcarbamate. To a solution of tert-butyl 4-(3-(dimethylcarbamoyloxy)-phenylcarbamoyl)-4-(2-methoxyethoxy)-piperidine-1-carboxylate from step C (150 mg, 0.322 mmol) in methanol (2 mL) was added HCl (4 M solution in dioxane, 0.3 mL). The reaction was heated at 50° C. for 1 hour, and then concentrated under vacuum to provide the title compound as the hydrochloride salt. MS (ES+) [M+H]$^+$=366.3.

E. Preparation of 3-(4-(2-methoxyethoxy)-1-(5-methyl-7H-pyrrolo[2,3-d]pyrimidin-4-yl)piperidine-4-carboxamido)phenyl dimethylcarbamate. To a solution of 3-(4-(2-methoxyethoxy)piperidine-4-carboxamido)phenyl dimethylcarbamate from step D, and N,N-diisopropylethylamine (0.28 mL, 1.6 mmol) in isopropanol (1.0 mL) was added 4-chloro-5-methyl-7H-pyrrolo[2,3-d]pyrimidine (55 mg, 0.322 mmol). The reaction mixture was heated to 110° C. in a sealed high-pressure vial for 17 h, during which time the mixture became homogenous. The mixture was concentrated under vacuum and purified by prep HPLC (30×100 mm C18 column, 5-100% acetonitrile:water (10 mM NH$_4$OAc), 15 min, 45 mL/min) to afford the title compound (17.4 mg) as a white solid.

$^1$H NMR (400 MHz, CD$_3$OD) δ ppm 8.20 (s, 1H), 7.51 (t, J=2.02 Hz, 1H), 7.40 (ddd, J=8.08, 2.02, 1.01 Hz, 1H), 7.33 (t, J=8.08 Hz, 1H), 6.98-7.02 (m, 1H), 6.89 (ddd, J=7.83, 2.27, 1.01 Hz, 1H), 3.92-4.01 (m, 2H), 3.69 (br. s., 4H), 3.51 (s, 3H), 3.29-3.38 (m, 2H), 3.12 (s, 3H), 2.99 (s, 3H), 2.43 (d, J=1.01 Hz, 3H), 2.31 (dt, J=13.64, 4.29 Hz, 2H), 1.97-2.07 (m, 2H). MS (ES+) [M+H]$^+$=497.3.

6.27. Example 27

Synthesis of 3-(4-amino-1-(5-methyl-7H-pyrrolo[2,3-d]pyrimidin-4-yl)piperidine-4-carboxamido)phenyl dimethylcarbamate

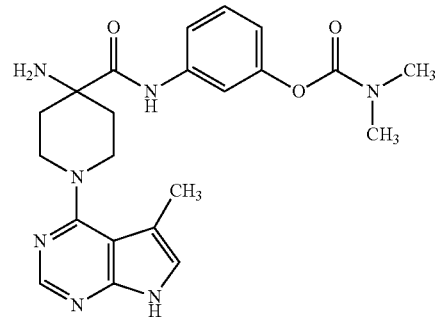

A. Preparation of tert-butyl 4-(tert-butoxycarbonylamino)-4-(3-(dimethylcarbamoyloxy)phenylcarbamoyl)piperidine-1-carboxylate. N-Boc-amino-(4-N-Boc-piperidinyl) carboxylic acid (0.114 g, 0.33 mmol), HATU (0.151 g, 0.40 mmol) and N,N-diisopropylethylamine (128 mg, 1.0 mmol) were combined in isopropyl acetate (2.3 mL) and stirred at room temperature for 15 minutes. 3-aminophenyl dimethylcarbamate (0.072 g, 0.40 mmol) was added, and the mixture heated at 80° C. for 1.5 hours. The reaction mixture was allowed to cool, diluted with EtOAc, washed with 2 N Na$_2$CO$_3$, 1 N HCl, and brine, and then dried over MgSO$_4$ and concentrated. Purification by silica gel chromatography (60% EtOAc/hexanes) gave the title compound (0.075 g, 45%) as a white solid. MS (ES+) [M+NH$_4$]$^+$=524.

B. Preparation of 3-(4-aminopiperidine-4-carboxamido)phenyl dimethylcarbamate. To a solution of tert-butyl 4-(tert-butoxycarbonylamino)-4-(3-(dimethylcarbamoyloxy)phenylcarbamoyl)piperidine-1-carboxylate from step A (0.141 g, 0.28 mmol) in MeOH (2 mL) was added HCl (4 N in dioxane, 0.21 mL, 0.84 mmol). The mixture was stirred at room temperature for 14 hours. Further equivalents of HCl/dioxane were added at this time, and the mixture stirred for a further 24 hours at room temperature. The solvent was removed under vacuum to afford the title compound (0.084 g, 98%), which was carried on crude. MS (ES+) [M+H]$^+$=307.

C. Preparation of 3-(4-amino-1-(5-methyl-7H-pyrrolo[2,3-d]pyrimidin-4-yl)piperidine-4-carboxamido)phenyl dimethylcarbamate. 3-(4-aminopiperidine-4-carboxamido)phenyl dimethylcarbamate from step B (0.109 g, 0.36 mmol), 4-chloro-5-methyl-7H-pyrrolo[2,3-c]pyrimidine (0.060 g, 0.36 mmol), and N,N-diisopropylethylamine (0.277 g, 2.14 mmol) were combined in isopropanol (5 mL) and heated in a sealed tube at 120° C. for 18 hours. The mixture was concentrated, and the residue was purification by silica gel chromatography (0-10% MeOH/CH$_2$Cl$_2$) to afford the title compound (0.085 g, 55%) as a white solid.

$^1$H NMR (400 MHz, CD$_3$OD) δ ppm 8.25 (s, 1H), 7.61 (m, 1H), 7.47 (m, 1H), 7.38 (m, 1H), 7.05 (d, J=1.0 Hz, 1H), 6.91 (m, 1H), 4.00 (m, 2H), 2.48 (m, 2H), 3.18 (s, 3H), 3.05 (s, 3H), 2.51 (s, 3H), 2.45 (m, 2H), 1.72 (m, 2H); MS (ES+) [M+H]$^+$= 438.

6.28. Example 28

Synthesis of 3-(4-(dimethylamino)-1-(5-methyl-7H-pyrrolo[2,3-d]pyrimidin-4-yl)piperidine-4-carboxamido)phenyl dimethylcarbamate

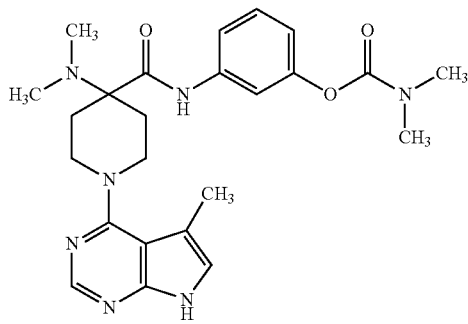

3-(4-amino-1-(5-methyl-7H-pyrrolo[2,3-d]pyrimidin-4-yl)piperidine-4-carboxamido)phenyl dimethylcarbamate from example 27, step C, (0.028 g, 0.064 mmol) was dissolved in MeOH (1 mL). Formaldehyde (37 wt % solution in H$_2$O, 0.15 mmol, 12 µl) was added followed by AcOH (0.26 mmol, 15 µl) and NaBH$_3$CN (0.008 g, 0.13 mmol). The mixture was stirred at room temperature for 2 hours before concentrating under vacuum. Purification by prep HPLC afforded the title compound (0.017 g, 57%) as a white solid.

$^1$H NMR (400 MHz, CD$_3$OD) δ ppm 8.21 (s, 1H), 7.56 (m, 1H), 7.46 (m, 1H), 7.37 (m, 1H), 7.03 (d, J=1.0 Hz, 1H), 6.92 (m, 1H), 4.08 (m, 2H), 3.47 (m, 2H), 3.17 (s, 3H), 3.04 (s, 3H), 2.48 (s, 3H), 2.40 (s, 6H), 2.26 (m, 2H), 2.09 (m, 2H); MS (ES+) [M+H]$^+$=466.

6.29. Example 29

Synthesis of 3-(4-((2-(1H-imidazol-5-yl)acetamido) methyl)-1-(5-methyl-7H-pyrrolo[2,3-d]pyrimidin-4-yl)piperidine-4-carboxamido)phenyl dimethylcarbamate

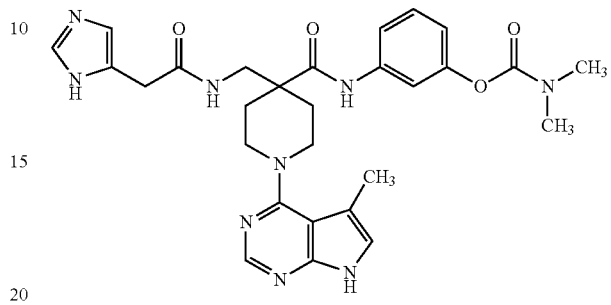

To a suspension of 2-(1H-imidazol-5-yl)acetic acid (0.238 g, 1.47 mmol) and HATU (0.372 g, 0.978 mmol) in CH$_2$Cl$_2$ (5 mL) was added N,N-diisopropylethylamine (0.51 mL, 2.93 mmol). The resulting solution was allowed to stir for 20 min. at room temperature. To this solution was added the acetate salt of 3-(4-(aminomethyl)-1-(5-methyl-7H-pyrrolo[2,3-d]pyrimidin-4-yl)piperidine-4-carboxamido)phenyl dimethylcarbamate (from example 20, 0.500 g, 0.978 mmol) and N,N-diisopropylethylamine (0.17 mL) in CH$_2$Cl$_2$ (5 mL). The reaction was allowed to stir at room temperature for 6 h, and then diluted with H$_2$O (10 mL) and CH$_2$Cl$_2$ (20 mL). The mixture was extracted with CH$_2$Cl$_2$ (2×10 mL), and the combined organics were washed with NaHCO$_3$ (10 mL) and brine (10 mL), dried over MgSO$_4$, and concentrated under vacuum. The residue was purified by flash chromatography (3-10% MeOH:CH$_2$Cl$_2$) to afford the title compound (0.393 g, 72% yield) as a white solid. This solid was suspended in water, and acetic acid was added until the solution became clear. This solution was frozen and lyophilized to the di-acetate salt of the title compound (0.477 g).

$^1$H NMR (400 MHz, MeOD-d$_6$) δ ppm 8.17 (s, 1H), 7.57 (d, J=0.76 Hz, 1H), 7.47 (t, J=2.02 Hz, 1H), 7.37 (ddd, J=1.01, 1.77, 8.08 Hz, 1H), 7.30 (t, J=8.08 Hz, 1H), 6.98 (d, J=1.01 Hz, 1H), 6.92 (s, 1H), 6.87 (ddd, J=1.01, 2.27, 8.08 Hz, 1H), 3.87 (ddd, J=3.28, 3.28, 14.15 Hz, 2H), 3.58 (s, 2H), 3.52 (s, 2H), 3.32-3.38 (m, 2H), 3.12 (s, 3H), 3.00 (s, 3H), 2.42 (d, J=0.76 Hz, 3H), 2.35-2.42 (m, 2H), 1.96 (s, 6H), 1.75-1.85 (m, 2H). MS (ES+) [M+H]=560.

6.30. Example 30

Additional Compounds

Using the procedures described herein and methods known in the art, the additional compounds listed below in Table 1 were prepared. The LIMK2 IC$_{50}$ data that is provided below for some of the compounds was determined using the assay described in Example 32.

TABLE 1

| Compound | MS (M + H)$^+$ | LIMK2 IC$_{50}$ |
|---|---|---|
| N-(3-(4-fluorophenoxy)phenyl)-4-methyl-1-(5-methyl-7H-pyrrolo[2,3-d]pyrimidin-4-yl)piperidine-4-carboxamide | 460 | <250 nM |
| N-(3-bromophenyl)-4-methyl-1-(5-methyl-7H-pyrrolo[2,3-d]pyrimidin-4-yl)piperidine-4-carboxamide | 428 | <250 nM |

TABLE 1-continued

| Compound | MS (M + H)$^+$ | LIMK2 IC$_{50}$ |
|---|---|---|
| N-(3-bromophenyl)-1-(5-chloro-7H-pyrrolo[2,3-d]pyrimidin-4-yl)-4-methylpiperidine-4-carboxamide | 450 | <250 nM |
| N-(3-(N-isopropylsulfamoyl)phenyl)-4-methyl-1-(5-methyl-7H-pyrrolo[2,3-d]pyrimidin-4-yl)piperidine-4-carboxamide | 471 | <250 nM |
| 4-allyl-N-(3-bromophenyl)-1-(5-methyl-7H-pyrrolo[2,3-d]pyrimidin-4-yl)piperidine-4-carboxamide | 456 | <250 nM |
| N-(4-methoxyphenyl)-4-methyl-1-(5-methyl-7H-pyrrolo[2,3-d]pyrimidin-4-yl)piperidine-4-carboxamide | 380 | <250 nM |
| 4-allyl-N-(3-tert-butylphenyl)-1-(5-methyl-7H-pyrrolo[2,3-d]pyrimidin-4-yl)piperidine-4-carboxamide | 432 | <250 nM |
| 4-methyl-1-(5-methyl-7H-pyrrolo[2,3-d]pyrimidin-4-yl)-N-(3-(trifluoromethyl)phenyl)piperidine-4-carboxamide | 418 | <250 nM |
| 4-allyl-N-(3-(4-fluorophenoxy)phenyl)-1-(5-methyl-7H-pyrrolo[2,3-d]pyrimidin-4-yl)piperidine-4-carboxamide | 486 | <250 nM |
| 4-allyl-N-(3-fluorophenyl)-1-(5-methyl-7H-pyrrolo[2,3-d]pyrimidin-4-yl)piperidine-4-carboxamide | 394 | <250 nM |
| 4-allyl-N-(3-methoxyphenyl)-1-(5-methyl-7H-pyrrolo[2,3-d]pyrimidin-4-yl)piperidine-4-carboxamide | 406 | <250 nM |
| 3-(4-allyl-1-(5-methyl-7H-pyrrolo[2,3-d]pyrimidin-4-yl)piperidine-4-carboxamido)phenyl dimethylcarbamate | 463 | <250 nM |
| 3-(4-isopropyl-1-(5-methyl-7H-pyrrolo[2,3-d]pyrimidin-4-yl)piperidine-4-carboxamido)phenyl dimethylcarbamate | 465 | <250 nM |
| 4-methyl-1-(5-methyl-7H-pyrrolo[2,3-d]pyrimidin-4-yl)-N-phenylpiperidine-4-carboxamide | 350 | <250 nM |
| 3-(1-(5-methyl-7H-pyrrolo[2,3-d]pyrimidin-4-yl)-4-propylpiperidine-4-carboxamido)phenyl dimethylcarbamate | 465 | <250 nM |
| N-(3-bromo-4-fluorophenyl)-4-methyl-1-(5-methyl-7H-pyrrolo[2,3-d]pyrimidin-4-yl)piperidine-4-carboxamide | 447 | <250 nM |
| 4-methyl-1-(5-methyl-7H-pyrrolo[2,3-d]pyrimidin-4-yl)-N-(3-(morpholinosulfonyl)phenyl)piperidine-4-carboxamide | 499 | <250 nM |
| 4-methyl-1-(5-methyl-7H-pyrrolo[2,3-d]pyrimidin-4-yl)-N-m-tolylpiperidine-4-carboxamide | 364 | <250 nM |
| N-(3-isobutyramidophenyl)-4-methyl-1-(5-methyl-7H-pyrrolo[2,3-d]pyrimidin-4-yl)piperidine-4-carboxamide | 435 | <250 nM |
| N-(3-(2-(dimethylamino)-2-oxoethyl)phenyl)-4-methyl-1-(5-methyl-7H-pyrrolo[2,3-d]pyrimidin-4-yl)piperidine-4-carboxamide | 435 | <250 nM |
| 3-(4-methyl-1-(5-methyl-7H-pyrrolo[2,3-d]pyrimidin-4-yl)piperidine-4-carboxamido)phenyl morpholine-4-carboxylate | 479 | <250 nM |
| 3-(1-(5-methyl-7H-pyrrolo[2,3-d]pyrimidin-4-yl)-4-((3-methylureido)methyl)piperidine-4-carboxamido)phenyl dimethylcarbamate | 509 | |
| 3-(4-((2-(dimethylamino)ethoxy)methyl)-1-(5-methyl-7H-pyrrolo[2,3-d]pyrimidin-4-yl)piperidine-4-carboxamido)phenyl dimethylcarbamate | 524 | |
| 3-(4-cyano-1-(5-methyl-7H-pyrrolo[2,3-d]pyrimidin-4-yl)piperidine-4-carboxamido)phenyl dimethylcarbamate | 448 | |
| 3-(4-(acetamidomethyl)-1-(5-methyl-7H-pyrrolo[2,3-d]pyrimidin-4-yl)piperidine-4-carboxamido)phenyl dimethylcarbamate | 494 | <250 nM |
| 3-(4-(2-aminoethylamino)-1-(5-methyl-7H-pyrrolo[2,3-d]pyrimidin-4-yl)piperidine-4-carboxamido)phenyl dimethylcarbamate | 481 | <250 nM |
| 3-(4-(2-(tert-butoxycarbonylamino)ethylamino)-1-(5-methyl-7H-pyrrolo[2,3-d]pyrimidin-4-yl)piperidine-4-carboxamido)phenyl dimethylcarbamate | 581 | <250 nM |
| 3-(4-(2-(benzyloxy)ethylamino)-1-(5-methyl-7H-pyrrolo[2,3-d]pyrimidin-4-yl)piperidine-4-carboxamido)phenyl dimethylcarbamate | 572 | <250 nM |
| 3-(4-cyano-1-(5-methyl-7H-pyrrolo[2,3-d]pyrimidin-4-yl)piperidine-4-carboxamido)phenyl dimethylcarbamate | 448 | <250 nM |
| 3-(4-(2-hydroxyethylamino)-1-(5-methyl-7H-pyrrolo[2,3-d]pyrimidin-4-yl)piperidine-4-carboxamido)phenyl dimethylcarbamate | 482 | <250 nM |
| 3-(4-((1-benzyl-1H-tetrazol-5-yl)methyl)-1-(5-methyl-7H-pyrrolo[2,3-d]pyrimidin-4-yl)piperidine-4-carboxamido)phenyl dimethylcarbamate | 595 | <250 nM |
| 3-(4-((1H-tetrazol-5-yl)methyl)-1-(5-methyl-7H-pyrrolo[2,3-d]pyrimidin-4-yl)piperidine-4-carboxamido)phenyl dimethylcarbamate | 505 | <250 nM |
| 3-(1-(5-methyl-7H-pyrrolo[2,3-d]pyrimidin-4-yl)-4-(methylsulfonamidomethyl)piperidine-4-carboxamido)phenyl dimethylcarbamate | 530 | <250 nM |

TABLE 1-continued

| Compound | MS (M + H)⁺ | LIMK2 IC$_{50}$ |
|---|---|---|
| 3-(4-((N,N-dimethylsulfamoylamino)methyl)-1-(5-methyl-7H-pyrrolo[2,3-d]pyrimidin-4-yl)piperidine-4-carboxamido)phenyl dimethylcarbamate | 559 | <250 nM |
| 3-(4-((methoxycarbonylaminomethyl)-1-(5-methyl-7H-pyrrolo[2,3-d]pyrimidin-4-yl)piperidine-4-carboxamido)phenyl dimethylcarbamate | 510 | <250 nM |
| 3-(4-((1-methyl-1H-pyrazole-4-carboxamido)methyl)-1-(5-methyl-7H-pyrrolo[2,3-d]pyrimidin-4-yl)piperidine-4-carboxamido)phenyl dimethylcarbamate | 560 | <250 nM |
| 3-(1-(5-methyl-7H-pyrrolo[2,3-d]pyrimidin-4-yl)-4-((morpholine-4-carboxamido)methyl)piperidine-4-carboxamido)phenyl dimethylcarbamate | 565 | <250 nM |
| 3-(1-(5-methyl-7H-pyrrolo[2,3-d]pyrimidin-4-yl)-4-(ureidomethyl)piperidine-4-carboxamido)phenyl dimethylcarbamate | 495 | <250 nM |
| 3-(4-((3-hydroxy-2-(hydroxymethyl)-2-methylpropanamido)methyl)-1-(5-methyl-7H-pyrrolo[2,3-d]pyrimidin-4-yl)piperidine-4-carboxamido)phenyl dimethylcarbamate | 568 | <250 nM |
| 3-(4-((1-tert-butoxycarbonylaminocyclopropanecarboxamido)methyl)-1-(5-methyl-7H-pyrrolo[2,3-d]pyrimidin-4-yl)piperidine-4-carboxamido)phenyl dimethylcarbamate | 635 | <250 nM |
| 3-(4-((2-aminoacetamido)methyl)-1-(5-methyl-7H-pyrrolo[2,3-d]pyrimidin-4-yl)piperidine-4-carboxamido)phenyl dimethylcarbamate | 509 | <250 nM |
| 3-(4-((2-(dimethylamino)acetamido)methyl)-1-(5-methyl-7H-pyrrolo[2,3-d]pyrimidin-4-yl)piperidine-4-carboxamido)phenyl dimethylcarbamate | 537 | <250 nM |
| 3-(1-(5-methyl-7H-pyrrolo[2,3-d]pyrimidin-4-yl)-4-((sulfamoylamino)methyl)piperidine-4-carboxamido)phenyl dimethylcarbamate | 531 | <250 nM |
| 3-(1-(5-methyl-7H-pyrrolo[2,3-d]pyrimidin-4-yl)-4-(2H-tetrazol-5-yl)piperidine-4-carboxamido)phenyl dimethylcarbamate | 491 | <250 nM |
| 3-(4-((1H-imidazol-2-yl)methyl)-1-(5-methyl-7H-pyrrolo[2,3-d]pyrimidin-4-yl)piperidine-4-carboxamido)phenyl dimethylcarbamate | 503 | <250 nM |
| 3-(4-((1-aminocyclopropanecarboxamido)methyl)-1-(5-methyl-7H-pyrrolo[2,3-d]pyrimidin-4-yl)piperidine-4-carboxamido)phenyl dimethylcarbamate | 535 | <250 nM |
| (S)-3-(4-((2-amino-3-(1H-imidazol-4-yl)propanamido)methyl)-1-(5-methyl-7H-pyrrolo[2,3-d]pyrimidin-4-yl)piperidine-4-carboxamido)phenyl dimethylcarbamate | 589 | <250 nM |
| 4-(aminomethyl)-1-(5-methyl-7H-pyrrolo[2,3-d]pyrimidin-4-yl)-N-(3-(oxazol-5-yl)phenyl)piperidine-4-carboxamide | 432 | <250 nM |
| 3-(1-(5-methyl-7H-pyrrolo[2,3-d]pyrimidin-4-yl)-4-(morpholinomethyl)piperidine-4-carboxamido)phenyl dimethylcarbamate | 522 | <250 nM |
| (S)-3-(4-((2-amino-3-hydroxypropanamido)methyl)-1-(5-methyl-7H-pyrrolo[2,3-d]pyrimidin-4-yl)piperidine-4-carboxamido)phenyl dimethylcarbamate | 539 | <250 nM |
| (S)-3-(4-((2,5-diaminopentanamido)methyl)-1-(5-methyl-7H-pyrrolo[2,3-d]pyrimidin-4-yl)piperidine-4-carboxamido)phenyl dimethylcarbamate | 566 | <250 nM |
| 3-(4-(azidomethyl)-1-(5-methyl-7H-pyrrolo[2,3-d]pyrimidin-4-yl)piperidine-4-carboxamido)phenyl dimethylcarbamate | 478 | <250 nM |
| 4-(aminomethyl)-N-(3-hydroxyphenyl)-1-(5-methyl-7H-pyrrolo[2,3-d]pyrimidin-4-yl)piperidine-4-carboxamide | 381 | <250 nM |
| 3-(1-(5-methyl-7H-pyrrolo[2,3-d]pyrimidin-4-yl)-4-(2-morpholinoethyl)piperidine-4-carboxamido)phenyl dimethylcarbamate | 536 | <250 nM |
| dimethyl 1-((4-(3-(dimethylcarbamoyloxy)phenylcarbamoyl)-1-(5-methyl-7H-pyrrolo[2,3-d]pyrimidin-4-yl)piperidin-4-yl)methyl)-1H-1,2,3-triazole-4,5-dicarboxylate | 620 | <250 nM |
| 3-(4-((5-methyl-1H-pyrazole-3-carboxamido)methyl)-1-(5-methyl-7H-pyrrolo[2,3-d]pyrimidin-4-yl)piperidine-4-carboxamido)phenyl dimethylcarbamate | 560 | <250 nM |
| 3-(4-((2-(2-methoxyethoxy)acetamido)methyl)-1-(5-methyl-7H-pyrrolo[2,3-d]pyrimidin-4-yl)piperidine-4-carboxamido)phenyl dimethylcarbamate | 568 | <250 nM |
| 4-(aminomethyl)-1-(5-methyl-7H-pyrrolo[2,3-d]pyrimidin-4-yl)-N-m-tolylpiperidine-4-carboxamide | 379 | <250 nM |

TABLE 1-continued

| Compound | MS (M + H)+ | LIMK2 IC$_{50}$ |
|---|---|---|
| 4-(aminomethyl)-N-(3-chlorophenyl)-1-(5-methyl-7H-pyrrolo[2,3-d]pyrimidin-4-yl)piperidine-4-carboxamide | 399 | <250 nM |
| 4-(aminomethyl)-N-(3-methoxyphenyl)-1-(5-methyl-7H-pyrrolo[2,3-d]pyrimidin-4-yl)piperidine-4-carboxamide | 395 | <250 nM |
| 4-(aminomethyl)-N-(3-fluorophenyl)-1-(5-methyl-7H-pyrrolo[2,3-d]pyrimidin-4-yl)piperidine-4-carboxamide | 383 | <250 nM |
| 4-(aminomethyl)-N-(3-(isopropylcarbamoyl)phenyl)-1-(5-methyl-7H-pyrrolo[2,3-d]pyrimidin-4-yl)piperidine-4-carboxamide | 450 | <250 nM |
| 4-(aminomethyl)-N-(3-(dimethylcarbamoyl)phenyl)-1-(5-methyl-7H-pyrrolo[2,3-d]pyrimidin-4-yl)piperidine-4-carboxamide | 436 | <250 nM |
| 4-(aminomethyl)-N-(3-(2-(dimethylamino)-2-oxoethoxy)phenyl)-1-(5-methyl-7H-pyrrolo[2,3-d]pyrimidin-4-yl)piperidine-4-carboxamide | 466 | <250 nM |
| 3-(4-((3-methoxypropanamido)methyl)-1-(5-methyl-7H-pyrrolo[2,3-d]pyrimidin-4-yl)piperidine-4-carboxamido)phenyl dimethylcarbamate | 538 | <250 nM |
| 3-(4-((2-methoxyacetamido)methyl)-1-(5-methyl-7H-pyrrolo[2,3-d]pyrimidin-4-yl)piperidine-4-carboxamido)phenyl dimethylcarbamate | 524 | <250 nM |
| 4-(aminomethyl)-N-(3-(2-methoxyethoxy)phenyl)-1-(5-methyl-7H-pyrrolo[2,3-d]pyrimidin-4-yl)piperidine-4-carboxamide | 439 | <250 nM |
| 4-(aminomethyl)-1-(5-methyl-7H-pyrrolo[2,3-d]pyrimidin-4-yl)-N-(3-(trifluoromethyl)phenyl)piperidine-4-carboxamide | 433 | <250 nM |
| 4-(aminomethyl)-N-(3-cyanophenyl)-1-(5-methyl-7H-pyrrolo[2,3-d]pyrimidin-4-yl)piperidine-4-carboxamide | 390 | <250 nM |
| 3-(4-((2-(2,5-dioxoimidazolidin-4-yl)acetamido)methyl)-1-(5-methyl-7H-pyrrolo[2,3-d]pyrimidin-4-yl)piperidine-4-carboxamido)phenyl dimethylcarbamate | 592 | <250 nM |
| 4-(aminomethyl)-1-(5-methyl-7H-pyrrolo[2,3-d]pyrimidin-4-yl)-N-(2-(methylamino)benzo[d]oxazol-6-yl)piperidine-4-carboxamide | 435 | <500 nM |
| 4-(aminomethyl)-N-(2-(dimethylamino)benzo[d]oxazol-6-yl)-1-(5-methyl-7H-pyrrolo[2,3-d]pyrimidin-4-yl)piperidine-4-carboxamide | 449 | <500 nM |
| 3-(4-(aminomethyl)-1-(5-methyl-7H-pyrrolo[2,3-d]pyrimidin-4-yl)piperidine-4-carboxamido)phenyl diethylcarbamate | 480 | <250 nM |
| 3-(4-(aminomethyl)-1-(5-methyl-7H-pyrrolo[2,3-d]pyrimidin-4-yl)piperidine-4-carboxamido)phenyl pyrrolidine-1-carboxylate | 478 | <250 nM |
| 4-(aminomethyl)-N-(3-bromophenyl)-1-(5-methyl-7H-pyrrolo[2,3-d]pyrimidin-4-yl)piperidine-4-carboxamide | 443 | <250 nM |
| 4-(aminomethyl)-N-(3-isopropoxyphenyl)-1-(5-methyl-7H-pyrrolo[2,3-d]pyrimidin-4-yl)piperidine-4-carboxamide | 423 | <250 nM |
| 4-(aminomethyl)-N-(3-tert-butylphenyl)-1-(5-methyl-7H-pyrrolo[2,3-d]pyrimidin-4-yl)piperidine-4-carboxamide | 421 | <250 nM |
| (R)-3-(1-(5-methyl-7H-pyrrolo[2,3-d]pyrimidin-4-yl)-4-((pyrrolidine-2-carboxamido)methyl)piperidine-4-carboxamido)phenyl dimethylcarbamate | 549 | |
| 3-(1-(5-methyl-7H-pyrrolo[2,3-d]pyrimidin-4-yl)-4-((methylamino)methyl)piperidine-4-carboxamido)phenyl dimethylcarbamate | 466 | |
| 3-(4-(2-(dimethylamino)ethyl)-1-(5-methyl-7H-pyrrolo[2,3-d]pyrimidin-4-yl)piperidine-4-carboxamido)phenyl diethylcarbamate | 522 | |
| 4-(2-(dimethylamino)ethyl)-N-(3-isopropoxyphenyl)-1-(5-methyl-7H-pyrrolo[2,3-d]pyrimidin-4-yl)piperidine-4-carboxamide | 465 | |
| N-(3-tert-butylphenyl)-4-(2-(dimethylamino)ethyl)-1-(5-methyl-7H-pyrrolo[2,3-d]pyrimidin-4-yl)piperidine-4-carboxamide | 463 | |
| 3-(1-(5-methyl-7H-pyrrolo[2,3-d]pyrimidin-4-yl)-4-((5-oxopyrrolidine-2-carboxamido)methyl)piperidine-4-carboxamido)phenyl dimethylcarbamate | 563 | |
| N-(3-bromophenyl)-4-(2-(dimethylamino)ethyl)-1-(5-methyl-7H-pyrrolo[2,3-d]pyrimidin-4-yl)piperidine-4-carboxamide | 485 | |
| 4-(2-(dimethylamino)ethyl)-1-(5-methyl-7H-pyrrolo[2,3-d]pyrimidin-4-yl)-N-(3-(trifluoromethyl)phenyl)piperidine-4-carboxamide | 475 | |

TABLE 1-continued

| Compound | MS (M + H)+ | LIMK2 IC$_{50}$ |
|---|---|---|
| 3-(4-(aminomethyl)-1-(5-methyl-7H-pyrrolo[2,3-d]pyrimidin-4-yl)piperidine-4-carboxamido)phenyl diisopropylcarbamate | 508 | |
| 4-(aminomethyl)-N-(4-(aminomethyl)phenyl)-1-(5-methyl-7H-pyrrolo[2,3-d]pyrimidin-4-yl)piperidine-4-carboxamide | 394 | |
| 4-(aminomethyl)-N-(4-((dimethylamino)methyl)phenyl)-1-(5-methyl-7H-pyrrolo[2,3-d]pyrimidin-4-yl)piperidine-4-carboxamide | 422 | |
| 4-(aminomethyl)-N-(3-ethoxyphenyl)-1-(5-methyl-7H-pyrrolo[2,3-d]pyrimidin-4-yl)piperidine-4-carboxamide | 409 | |
| 4-(aminomethyl)-N-(3-isobutoxyphenyl)-1-(5-methyl-7H-pyrrolo[2,3-d]pyrimidin-4-yl)piperidine-4-carboxamide | 437 | |
| (R)-4-(aminomethyl)-1-(5-methyl-7H-pyrrolo[2,3-d]pyrimidin-4-yl)-N-(3-(tetrahydrofuran-3-yloxy)phenyl)piperidine-4-carboxamide | 451 | |
| 4-(aminomethyl)-N-(3-(cyclopentyloxy)phenyl)-1-(5-methyl-7H-pyrrolo[2,3-d]pyrimidin-4-yl)piperidine-4-carboxamide | 449 | |
| 4-(aminomethyl)-1-(5-methyl-7H-pyrrolo[2,3-d]pyrimidin-4-yl)-N-(3-(tetrahydro-2H-pyran-4-yloxy)phenyl)piperidine-4-carboxamide | 465 | |
| 4-(aminomethyl)-N-(3-((3R,4R)-4-hydroxytetrahydrofuran-3-yloxy)phenyl)-1-(5-methyl-7H-pyrrolo[2,3-d]pyrimidin-4-yl)piperidine-4-carboxamide | 467 | |

6.31. Expression and Purification of LIMK2

LIMK2 was expressed using the BAC-to-BAC® Baculovirus Expression System (Invitrogen). Recombinant baculovirus was made according to the manufacturer's directions as set forth in the instruction manual. Briefly, the plasmids (pFactBac1 or pFastBacHT) carrying the LIMK2 inserts were transformed into MAX efficiency DH10Bac competent E. coli to generate a recombinant bacmid. The DH10Bac E. coli host strain contains a baculovirus shuttle vector (bacmid) with a mini-attTn7 target site and a helper plasmid, and allows generation of a recombinant bacmid following transposition between the mini-Tn7 element on the pFastBac vector and the min-attTn7 target site on the bacmid. The transposition reaction occurs in the presence of transposition proteins supplied by the helper plasmid. Cells were plated and the white colonies picked for bacmid isolation as described in the instruction manual.

The isolated bacmid DNA was transfected into SF9 cells to generate a recombinant baculovirus, and virus was collected five days after transfection. Virus was amplified in T75 flasks at a multiplicity of infection (MOI) of 0.2. The amplified virus was used to infect SF9 cells at a MOI 5 for protein expression.

For small scale purification of the LIMK2 constructs, a 50 ml culture of Sf9 cells infected with the recombinant baculovirus was used. The cells were harvested by centrifugation for 5 minutes at 500×g. The cells were then resuspended in lysis buffer (5 volumes per gram of cells). A typical lysis buffer contains the following: 50 mM HEPES (pH 8.0), 300 mM KCl, 10% glycerol, 1% NP-40, 15 mM imidazole, 1 mM benzamidine, and Roche complete protease inhibitors (1 tablet per 50 ml of cell lysate). The cellular suspension was lysed by one passage through a Microfluidics Microfluidizer M-110Y at a liquid pressure of 14,000 to 20,000 psi followed by centrifugation of the lysate at 60,000×g for 15 minutes at 4° C.

The supernatant was then loaded directly onto a chromatography matrix containing Cobalt ion covalently attached to nitrilotriacetic acid NTA. The chromatography matrix was equilibrated in the same buffer as the protein loading solution. The ion charged resin typically has a binding capacity equivalent to 5 to 10 mg histidine-tagged protein per ml of packed resin. The amount of extract that can be loaded onto the column depends on the amount of soluble histidine-tagged protein in the extract. The column was then washed in a stepwise fashion, first with: 50 mM HEPES (pH 8.0), 300 mM KCl, 10% glycerol, 1% NP-40, 15 mM imidazole, 1 mM benzamidine; second, with 20 mM HEPES (pH 8.0), 500 mM KCl, 10% glycerol, and 20 mM imidazole; third, with 20 mM HEPES (pH 8.0), 100 mM KCl, 10% glycerol, and 20 mM imidazole; followed by elution with 250 mM imidazole in the same buffer. The LIMK2 protein solution was then analyzed by SDS-PAGE and Western blot using commercial antibodies directed to both the carboxyl terminus and internal catalytic domains of the protein. For storage purposes the protein was dialyzed into 50 mM Tris (pH 7.5), 150 mM NaCl, 0.1% BME, 0.03% Brij-35, and 50% glycerol.

Large scale LIMK2 purification was done in a Wave Bioreactor (Wave Biotech) with 10 L culture volumes. 10 L of cell culture at 2-3×10$^6$ viable cells/mL were infected at an MOI=5 pfu/cell and harvested at 48 hours post infection.

6.32. In Vitro LIMK2 Inhibition Assay

An in vitro assay used to identify LIMK2 inhibitors was developed. The analytical readout was the incorporation of $^{33}$P from ATP substrate into immobilized myelin basic protein coated flash plates (Perkin Elmer Biosciences), which were counted on a scintillation counter equipped with a plate reader (TopCount, Packard Bioscience, Meriden, Conn.). Using 384 well flat MBP flashplates, total assay volume was 50 µl. The HTS program utilized a Biomek FX for dilution.

For each assay, the ingredients and conditions were as follows: 200 ng of enzyme was incubated in assay buffer (1× assay buffer contains 30 mM HEPES (pH 8.0), 5 mM DTT, and 10 mM MgCl$_2$), 10 µM ATP, 0.2 µCi [gamma-$^{33}$P]-ATP and 10 µM of potential inhibitory compound. The reaction was incubated at room temperature for 60 minutes, washed 3 times with 75 µl of stop/wash buffer (1× stop/was buffer contains 50 mM EDTA and 20 mM Tris (pH 7.4)), and then the plates were read on the scintillation counter. Different concentrations of staurosporine (400 nM, 200 nM, 100 nM and 50 nM; purchased from BIOMOL (Plymouth Meeting, Pa.)) were used as controls on each plate.

6.33. Dexamethasone-Induced Ocular Hypertension Model

Twenty eight day mouse Alzet mini-osmotic pumps (DURECT Corp., Cupertino, Calif.) were filled with a solution of water soluble dexamethasone (dex) in PBS (Sigma, St. Louis, Mo.) so that they would release roughly 0.1 mg of dex per day. Once the pumps were filled with the dex, the pumps were allowed to equilibrate in PBS at 37° C. for 60 hours. The equilibrated pumps were surgically placed subcutaneously on the backs of wild-type C57:129 F2 hybrid mice weighing between 25 and 35 grams. Surgical incisions were sutured with 5-0 braided silk (ROBOZ, Gaithersburg, Md.) and treated with antibiotic ointment throughout the entire duration of study. Surgical incisions were glued with TissueMend II (Webster Veterinary, Houston, Tex.). Analgesic (buprenorphine) was given through IP injection the day of surgery and 24 hours after surgery. Intraocular pressure (IOP) was measured on these mice using a TonoLab (Colonial Medical Supply Co., Franconia, N.H.) tonometer. Mice were mildly sedated with isoflurane and topically anesthetized with 0.5% proparacaine (Akorn, Buffalo Grove, Ill.) before IOP measurements were taken. Baseline IOP was measured 1 day prior to mini-pump implantation. After mini-pump implantation, IOP measurements were taken 2-3 times per week for 4 weeks. Pharmacology studies with potential ocular hypotensive compounds were performed between 21 and 28 days after implantation.

6.34. In Vivo Effects

Compounds of the invention were then tested in the mouse ocular hypertensive model, described above. The effects of four compounds of the invention topically administered to the eyes of the mice are described below in Table 2:

TABLE 2

| Compound | Dose$^a$ | Formulation$^b$ | Change in IOP (Number of Studies)$^c$ | | |
|---|---|---|---|---|---|
| | | | 2 hours | 4 hours | 6 hours |
| A | 30 | 1 | −4.4 | −1.6 | Not tested |
| A | 3 | 1 | −4.2 (7) | −2.6 (7) | −1.3 (4) |
| A | 0.3 | 1 | −2.0 (3) | −1.6 (3) | −0.1 |
| A | 3 | 2 | −4.6 | −2.6 | −1.4 |
| B | 30 | 2 | −4.1 | −2.5 | −.03 |
| B | 3 | 2 | −3.4 | −2.2 | −0.3 |
| C | 3 | 3 | −3.5 (2) | −0.9 (2) | −0.5 (2) |
| D | 3 | 3 | −1.8 | −0.8 | Not tested |
| D | 0.3 | 3 | −2.2 | −0.4 | Not tested |

$^a$Microgram per eye.
$^b$Ophthalmically acceptable excipients were used to make different formulations. The pH of formulation 1 was 7.2; the pH of formulation 2 was 7.2; and the pH of formulation 3 was 6.0.
$^c$Times are hours after dosing.

The effect of compound A was compared to that of timolol in the hypertensive model. As shown in FIG. 1, the topical administration of 3 μg per eye of compound A yielded substantially the effect as the topical administration of 15 μg per eye of timolol.

All publications (e.g., patents and patent applications) cited above are incorporated herein by reference in their entireties.

What is claimed is:

1. A method of lowering intraocular pressure in a patient, which comprises administering to a patient in need thereof a therapeutically or prophylactically effective amount of a compound of the formula:

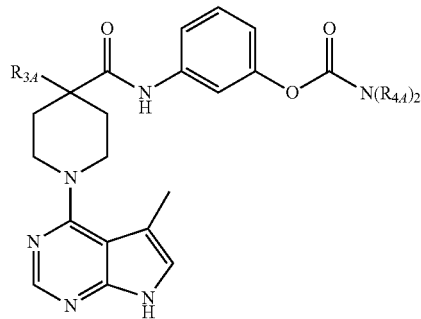

or a pharmaceutically acceptable salt thereof, wherein:
$R_{3A}$ is cyano, $C(O)R_{3C}$, $CO_2R_{3C}$, $CON(R_{3C})_2$, or optionally substituted alkyl, alkylaryl, alkylheterocycle, aryl, heteroalkyl, heteroalkylaryl, heteroalkylheterocycle, or heterocycle;
each $R_{3C}$ is independently optionally substituted alkyl, aryl or heterocycle; and
each $R_{4A}$ is independently hydrogen or optionally substituted alkyl or heteroalkyl.

2. The method of claim 1, wherein $R_{3A}$ is heteroalkyl.

3. The method of claim 2, wherein $R_{3A}$ is aminomethyl, (dimethylamino)methyl, or (dimethylamino)ethyl.

4. The method of claim 1, wherein at least one $R_{4A}$ is methyl.

5. The method of claim 1, wherein the compound is 3-(4-(aminomethyl)-1-(5-methyl-7H-pyrrolo[2,3-d]pyrimidin-4-yl)piperidine-4-carboxamido)phenyl dimethylcarbamate.

6. The method of claim 1, wherein the compound is administered in a pharmaceutical formulation comprising a liquid vehicle suitable for ophthalmic administration.

7. A method of lowering intraocular pressure in a patient, which comprises administering to a patient in need thereof a therapeutically effective amount of a pharmaceutical formulation comprising 3-(4-(aminomethyl)-1-(5-methyl-7H-pyrrolo[2,3-d]pyrimidin-4-yl)piperidine-4-carboxamido)phenyl dimethylcarbamate and a liquid vehicle suitable for ophthalmic administration.

* * * * *